US008828392B2

(12) United States Patent
Lichenstein et al.

(10) Patent No.: US 8,828,392 B2
(45) Date of Patent: Sep. 9, 2014

(54) HISTONE DEACETYLASE (HDAC) INHIBITORS (PXD101) FOR THE TREATMENT OF CANCER ALONE OR IN COMBINATION WITH CHEMOTHERAPEUTIC AGENT

(75) Inventors: Henri Lichenstein, Branford, CT (US); Nicholas Edwards, Abingdon (GB); James Ritchie, Abingdon (GB); Kamille Dumong Petersen, Copenhagen (DK); Jane Plumb, Glasglow (GB)

(73) Assignee: TopoTarget UK Limited, Abingdon, Oxfordshire (GB)

( * ) Notice: Subject to any disclaimer, the term of this patent is extended or adjusted under 35 U.S.C. 154(b) by 0 days.

(21) Appl. No.: 12/093,069

(22) PCT Filed: Nov. 10, 2006

(86) PCT No.: PCT/GB2006/004215
§ 371 (c)(1),
(2), (4) Date: May 8, 2008

(87) PCT Pub. No.: WO2007/054719
PCT Pub. Date: May 18, 2007

(65) Prior Publication Data
US 2008/0274120 A1 Nov. 6, 2008

Related U.S. Application Data

(60) Provisional application No. 60/735,701, filed on Nov. 10, 2005.

(51) Int. Cl.
| A61K 39/395 | (2006.01) |
| A01N 37/28 | (2006.01) |
| C12N 5/02 | (2006.01) |
| C12N 5/0781 | (2010.01) |
| C12N 5/09 | (2010.01) |
| A61K 31/10 | (2006.01) |
| A61K 31/65 | (2006.01) |
| A61K 31/573 | (2006.01) |
| A61K 31/475 | (2006.01) |
| A61K 45/06 | (2006.01) |
| A61K 31/196 | (2006.01) |

(52) U.S. Cl.
CPC .............. *A61K 31/10* (2013.01); *A61K 31/65* (2013.01); *A61K 31/573* (2013.01); *A61K 31/475* (2013.01); *A61K 45/06* (2013.01); *A61K 31/196* (2013.01)
USPC .............. 424/144.1; 424/153.1; 424/156.1

(58) Field of Classification Search
None
See application file for complete search history.

(56) References Cited

U.S. PATENT DOCUMENTS

| 4,642,316 | A | 2/1987 | Fawzi et al. |
| 6,071,923 | A | 6/2000 | Nudelman et al. |
| 6,342,219 | B1 | 1/2002 | Thorpe et al. |
| 6,541,661 | B1 | 4/2003 | Delorme et al. |
| 6,656,905 | B1 | 12/2003 | Mori et al. |
| 6,888,027 | B2 | 5/2005 | Watkins et al. |
| 7,183,298 | B2 | 2/2007 | Watkins et al. |
| RE39,850 | E | 9/2007 | Delorme et al. |
| 7,375,137 | B2 | 5/2008 | Bacopoulos et al. |
| 7,407,988 | B2 | 8/2008 | Kalvinsh et al. |
| 7,465,731 | B2 | 12/2008 | Ishibashi et al. |
| 7,491,748 | B2 | 2/2009 | Tani et al. |
| 7,495,022 | B2 | 2/2009 | Kim et al. |
| 7,557,140 | B2 | 7/2009 | Kalvinsh et al. |
| 2003/0170319 | A1 | 9/2003 | Netke et al. |
| 2003/0235588 | A1 | 12/2003 | Richon et al. |
| 2004/0018968 | A1 | 1/2004 | Sgouros et al. |
| 2004/0072735 | A1 | 4/2004 | Richon et al. |
| 2004/0077726 | A1* | 4/2004 | Watkins et al. ............... 514/575 |
| 2004/0092598 | A1 | 5/2004 | Watkins et al. |
| 2004/0127523 | A1 | 7/2004 | Bacopoulos et al. |
| 2004/0132825 | A1 | 7/2004 | Bacopoulos et al. |
| 2004/0198830 | A1 | 10/2004 | Watkins et al. |

(Continued)

FOREIGN PATENT DOCUMENTS

| EP | 0787742 | 8/1997 |
| EP | 1293205 | 3/2003 |

(Continued)

OTHER PUBLICATIONS

Moradei et al. (Curr. Med. Chem.—Anti-Cancer Agents 2005; 5: 529-560).*

(Continued)

*Primary Examiner* — Karen Canella
(74) *Attorney, Agent, or Firm* — Greenberg Traurig, LLP

(57) ABSTRACT

The present invention relates generally to methods for treating cancer. In one respect, the present invention relates to a method of treating a hematological cancer (e.g., multiple myeloma, leukemia, lymphoma) comprising administering to a patient in need thereof a therapeutically effective amount of a histone deacetylase inhibitor, for example, a histone deacetylase (HDAC) inhibitor as described herein, for example, PXD-101. In another respect, the present invention relates to a method of treating cancer (e.g., solid tumor cancer, e.g., rectal cancer, colon cancer, ovarian cancer; hematological cancer, e.g., multiple myeloma, leukemia, lymphoma) comprising administering to a patient in need thereof, a first amount of a histone deacetylase (HDAC) inhibitor, for example, a histone deacetylase inhibitor as described herein, for example, PXD-101, and a second amount of an other chemotherapeutic agent, for example, an other chemotherapeutic agent selected from: an antibody against VEGF, AVASTIN® (bevacizumab), an antibody against CD20, rituximab, bortezomib, thalidomide, dexamethasone, vincristine, doxorubicin, and melphalan, wherein the first and second amounts together comprise a therapeutically effective amount.

3 Claims, 5 Drawing Sheets

(56) References Cited

U.S. PATENT DOCUMENTS

| | | |
|---|---|---|
| 2004/0220242 A1 | 11/2004 | Shapiro |
| 2004/0254220 A1 | 12/2004 | Bressi et al. |
| 2005/0085515 A1 | 4/2005 | Watkins et al. |
| 2005/0107445 A1 | 5/2005 | Watkins et al. |
| 2005/0119305 A1 | 6/2005 | Naka et al. |
| 2005/0124679 A1 | 6/2005 | Kim et al. |
| 2005/0222013 A1 | 10/2005 | Jung et al. |
| 2005/0245439 A1 | 11/2005 | Chung |
| 2005/0288227 A1 | 12/2005 | Marks et al. |
| 2006/0052599 A1 | 3/2006 | Ishibashi et al. |
| 2006/0058298 A1 | 3/2006 | Delorme et al. |
| 2006/0160897 A1 | 7/2006 | Pelicci et al. |
| 2006/0229237 A1 | 10/2006 | Chung et al. |
| 2006/0270016 A1 | 11/2006 | Holm |
| 2007/0004806 A1 | 1/2007 | Kalvinsh et al. |
| 2007/0037738 A1 | 2/2007 | Hentsch et al. |
| 2007/0054260 A1 | 3/2007 | Trepel et al. |
| 2007/0060614 A1 | 3/2007 | Bacopoulos et al. |
| 2007/0110719 A1 | 5/2007 | Holm |
| 2007/0148228 A1 | 6/2007 | Cumming et al. |
| 2007/0232528 A1 | 10/2007 | Franke |
| 2007/0292512 A1 | 12/2007 | Leonard et al. |
| 2008/0004311 A1 | 1/2008 | Hellberg |
| 2008/0045445 A1 | 2/2008 | Chen et al. |
| 2008/0119424 A1 | 5/2008 | Bernards et al. |
| 2008/0146623 A1 | 6/2008 | Deziel et al. |
| 2008/0161401 A1 | 7/2008 | Watkins et al. |
| 2008/0194690 A1 | 8/2008 | Bastin et al. |
| 2008/0207724 A1 | 8/2008 | Mink et al. |
| 2008/0213399 A1 | 9/2008 | Lichenstein et al. |
| 2008/0214547 A1 | 9/2008 | Srivastava et al. |
| 2008/0242648 A1 | 10/2008 | Ordentlich et al. |
| 2008/0249137 A1 | 10/2008 | Lin et al. |
| 2008/0249179 A1 | 10/2008 | Bacopoulos et al. |
| 2008/0274120 A1 | 11/2008 | Lichenstein et al. |
| 2008/0292616 A1 | 11/2008 | Bates et al. |
| 2009/0012175 A1 | 1/2009 | Bacopoulos et al. |
| 2009/0023149 A1 | 1/2009 | Knudsen |
| 2009/0036435 A1 | 2/2009 | Curry et al. |
| 2009/0048156 A1 | 2/2009 | Brodie et al. |
| 2009/0060873 A1 | 3/2009 | Sporn et al. |
| 2009/0098054 A1 | 4/2009 | Kufe |
| 2009/0105168 A1 | 4/2009 | Gruber et al. |
| 2009/0142337 A1 | 6/2009 | Squires |
| 2009/0186809 A1 | 7/2009 | Hentsch et al. |
| 2009/0232800 A1 | 9/2009 | Holm |
| 2009/0233902 A1 | 9/2009 | Vennemann et al. |
| 2009/0246169 A1 | 10/2009 | Vennemann et al. |
| 2009/0246198 A1 | 10/2009 | Dong et al. |
| 2009/0270497 A1 | 10/2009 | Buggy |
| 2009/0286862 A1 | 11/2009 | Narita et al. |
| 2009/0298924 A1 | 12/2009 | Davidson et al. |
| 2009/0311175 A1 | 12/2009 | Brose |

FOREIGN PATENT DOCUMENTS

| | | | |
|---|---|---|---|
| EP | 1426054 | | 6/2004 |
| JP | 10114681 | | 5/1998 |
| WO | WO 02/26696 | | 4/2002 |
| WO | WO 02/30879 | | 4/2002 |
| WO | WO0240717 | * | 5/2002 |
| WO | 02090534 | | 11/2002 |
| WO | 03066579 | | 8/2003 |
| WO | WO03/070234 | * | 8/2003 |
| WO | WO 03/075929 | | 9/2003 |
| WO | 03082288 | | 10/2003 |
| WO | 03087057 | | 10/2003 |
| WO | 03092686 | | 11/2003 |
| WO | 2004009536 | | 1/2004 |
| WO | 2004013130 | | 2/2004 |
| WO | 2004043962 | | 5/2004 |
| WO | 2004063146 | | 7/2004 |
| WO | 2004063169 | | 7/2004 |
| WO | 2004069803 | | 8/2004 |
| WO | 2004069823 | | 8/2004 |
| WO | 2004071400 | | 8/2004 |
| WO | 2004072047 | | 8/2004 |
| WO | WO 2004/064727 | | 8/2004 |
| WO | 2004074451 | | 9/2004 |
| WO | 2004082638 | | 9/2004 |
| WO | 2004087693 | | 10/2004 |
| WO | 2004092115 | | 10/2004 |
| WO | 2004103358 | | 12/2004 |
| WO | WO 2005/000901 | | 1/2005 |
| WO | WO 2005023179 A2 | * | 3/2005 |
| WO | 2005063806 | | 7/2005 |
| WO | WO 2006/012688 | | 2/2006 |
| WO | WO 2006/064121 | | 6/2006 |
| WO | WO 2006/082428 | | 8/2006 |
| WO | 2006120456 | | 11/2006 |
| WO | 2007049262 | | 5/2007 |
| WO | 2007110623 | | 10/2007 |
| WO | 2008090534 | | 7/2008 |

OTHER PUBLICATIONS

Granziero et al. (Eur. J. Immunol. 1999, 29:1127-1138).*
Byers, T. (CA Journal, vol. 49, No. 6, Nov./Dec. 1999).*
Rihova (Advanced Drug Delivery Reviews, 1998, vol. 29, pp. 273-289).*
American Cancer Society, Inc., "Cancer Facts and Figures 2003," (2003) 1-52.
Bast, R.C. et al., "Chapter 321: Ovarian Cancer," in Harrison's Principles of Internal Medicine, 13th edition, Isselbacher et al., eds., McGraw-Hill, New York (1994) 1853-1858.
Berge, S.M. et al., "Pharmaceutical Salts," J. Pharm. Sci. (1977) 66:1-19.
Budillon, A. et al., "Multiple-target drugs: inhibitors of heat shock protein 90 and of histone deacetylase," Current Drug Targets (2005) 6:337-351.
Finn, P.W. et al., "Novel sulfonamide derivatives as inhibitors of histone deacetylase," Helvetica Chimica Acta (2005) 88:1630-1657.
Jensen, P.B. et al., "Differential cytotoxicity of 19 anticancer agents in wild type and etoposide resistant small cell lung cancer cell lines," Br. J. Cancer (1993) 67:311-320.
Knies-Bamforth, U., "Fight against cancer taking centre stage in Boston," Drug Discovery Today (2004) 9(23):998-999.
Moredei, O. et al., "Histone deacetylase inhibitors: latest developments, trends and prospects," Curr. Med. Chem. (2005) 5:529-560.
Pauer, L.R. et al., "Phase I study of oral CI-994 in combination with carboplatin and paclitaxel in the treatment of patients with advanced solid tumors," Cancer Investigation (2004) 22(6):886-896.
Plumb, J.A. et al., "Epigenetic approaches to cancer therapy," Biochem. Soc. Transactions (2004) 32(6):1095-1097.
Ritchie, J. et al., "The histone deacetylase inhibitor PXC101 synergises with established chemotherapeutics to inhibit tumour cell proliferation and upregulate apoptosis in vitro," Clin. Cancer Res. (2003) 9(16) 2 Suppl.:6105S-6106S.
Shabbeer, S. et al., "Focus on deacetylation for therapeutic benefit," Idrugs 2005 United Kingdom (2005) 8(2):144-154.
Topotarget, "TopoTarget and CuraGen advance HDAC inhibitor PXD101 into Phase II clinical trials," Press Release dated Feb. 1, 2005 and retrieved 2006 from the internet (http://www.topotarget.com/multimedia/19_pressrelease_01022005.pdf) 2 pages.
"Topotarget aims for top of class," Bioventure View (2004) 19(13):11.
Wingo, P.A. et al., "Cancer statistics, 1995" CA Cancer Journal for Clinicians (1995) 45:8-30.
International Search Report and Written Opinion of the International Searching Authority for PCT/GB2006/004215 dated Apr. 26, 2007.
International Search Report and Written Opinion of the International Searching Authority for PCT/GB2006/000391 dated Jul. 8, 2006.
Hirano, A et al. "Application of Arginine to Increase the Solubility of Poorly Water-Soluble Compounds." J. of Proteomics & Bioinformatics, Proceedings of the Joint 2nd Pacific Rim International conference on Protein Science and 4th Asian-Oceania Human Proteome Organization, Cairns, Australia, Jun. 22-26, 2008; Abstract No. 220.
Hockly, E. et al., "Suberoylanilide hydroxamic acid, a histone deacetylase inhibitor, ameliorates motor deficits in a mouse model of

(56) References Cited

OTHER PUBLICATIONS

Huntington's disease," Proc. Natl. Acad. Sci. U.S.A., Feb. 18, 2003, vol. 100, No. 4, pp. 2041-2046.
Hoshikawa, Y. et al. "Trichostatin A induces Morphological Changes and Gelsolin Expression by Inhibiting Histone Deacetylase in Human Carcinoma Cell Lines." Exp. Cell. Res., 1994; 214(1): 189-197.
Howe, L. et al., "Histone Acetyltransferase Complexes and Their Link to Transcription." Crit. Rev. Eukaryot. Gene. Expr., 1999; 9(3-4): 231-243.
Iavarone et al. "E2F and Histone Deacetylase Mediate Transforming Growth Factor β Repression of cdc25A During Keratinocyte Cell Cycle Arrest." Mol. Cell Biol., 1999; 19(1):916-922.
Kao et al. "Isolation of a Novel Histone Deacetylase Reveals that Class I and Class II Deacetylases Promote SMRT-mediated Repression." Genes & Dev., 2000; 14(1): 55-66.
Kasim, N.A. et al. "Molecular Properties of WHO Essential Drugs and Provisional Biopharmaceutical Classification." Mol. Pharma, Sep. 2003; 1(1): 85-96.
Kim, Y.B. et al. "Oxamflatin is a Novel Antitumor Compound that Inhibits Mammalian Histone Deacetylase." Oncogene, 1999; 18(15): 2461-2470.
Kim, M.S. et al. "Histone Deacetylases Induce Angiogenesis by Negative Regulation of Tumour Suppressor Genes." Nature Medicine, 2001; 7(4):437-443.
Kimura et al. "Dual Modes of Action of Platelet-Derived Growth Factor and its Inhibition by Trichostatin-A for DNA Synthesis in Primary Cultured Smooth Muscle Cells of Rat Aorta." Biol. Pharm. Bull., 1994; 17(3):399-402.
Kitamura, K. et al. "Histone Deacetylase Inhibitor But Not Arsenic Trioxide Differentiates Acute Promyelocytic Leukemia Cells with t(11;17) in Combination with All-Trans Retinoic Acid." Br. J. Haematol., 2000; 108(4):696-702.
Kouzarides, T. "Histone Acetylases and Deacetylases in Cell Proliferation." Curr. Opin. Genet. Dev., 1999; 9(1):40-48.
Kuusisto et al. "Ubiquitin-Binding Protein p62 Expression is Induced during Apoptosis and Proteasomal Inhibition in Neuronal Cells." Biochem. Biophys. Res. Commun., 2001; 280(1): 223-228.
Laherty, C.D. et al. "Histone Deacetylases Associated with the mSin3 Corepressor Mediate Mad Transcriptional Repression." Cell, May 1997; 89(3): 349-356.
Lin, R.J. et al. "Role of the Histone Deacetylase Complex in Acute Promyelocytic Leukaemia." Nature, Feb. 1998; 391 (6669): 811-814.
McCaffrey et al. "Induction of γ-Globin by Histone Deacetylase Inhibitors." Blood, Sep. 1997; 90(5):2075-2083.
Mielnicki et al. "Epigenetic Regulation of Gelsolin Expression in Human breast Cancer Cells." Exp. Cell. Res., 1999; 249(1):161-176.
Mura, P. et al. "Ternary systems of faproxen with hydroxypropyl-beta-cyclodextrin and aminoacids." Intl. J. Pharm., 2003; 260(2):293-302.
Murata, T. et al., "Solubility of monoalkyl phosphate in water in the presence of arginine and triton, and solubilization of methyl yellow through the mixed micelle," Phosphorus Research Bulletin, (2008), vol. 22, pp. 41-47.
Ng, H.H. et al. "Histone Deacetylases: Silencers for Hire." Trends Biochem. Sci., 2000; 25(3):121-126.
Niki et al. "A Histone Deacetylase Inhibitor, Trichostatin A, Suppresses Myofibroblastic Differentiation of Rat Hepatic Stellate Cells in Primary Culture." Hepatol., 1999; 29(3):858-867.
Onishi, H. R. et al., "Antibacterial agents that inhibit lipid A biosynthesis," Science, Nov. 8, 1996, vol. 274, No. 5289, pp. 980-982.
Pazin, M.J. et al. "What's Up and down with Histone Deacetylation and Transcription?" Cell, 1997; 89(3):325-328.
Saunders, N. et al. "Histone Deacetylase Inhibitors as Potential Anti-Skin Cancer Agents." Cancer Res., 1999; 59(2):399-404.
Spencer, V.A. et al. "Role of Covalent Modifications of Histones in Regulating Gene Expression." Gene, 1999; 240(1):1-12.
Strickley, R. G., "Solubilizing excipients in oral and injectable formulations," Pharm. Res., Feb. 2004, vol. 21, No. 2, pp. 201-230.

Takahashi, I. et al. "Selective Inhibition of IL-2 Gene Expression by Trichostatin A, a Potent Inhibitor of Mammalian Histone Deacetylase." J. Antibiot. (Tokyo), 1996; 49(5):453-457.
Taunton, J. et al., "A mammalian histone deacetylase related to the yeast transcriptional regulator Rpd3p," Science, Apr. 19, 1996, vol. 272, No. 5260, pp. 408-411.
Tsuji et al. "A New Antifungal Antibiotic, Trichostatin." J. Antibiot. (Tokyo), 1976; 29(1):1-6.
Ueda, H. et al. "FR901228, a Novel Antitumor Bicyclic Depsipeptide Produced by *Chromobacterium violaceum* No. 968." J. Antibiot. (Tokyo), 1994; 47(3):315-323.
Van Den Wyngaert et al., "Cloning and characterization of human histone deacetylase 8," FEBS L., 2000, vol. 478, No. 1-2, pp. 77-83.
Vigushin et al. "Trichostatin A Is a Histone Deacetylase Inhibitor with Potent Antitumor Activity against Breast Cancer in vivo." Clin. Cancer Res., 2001; 7(4):971-976.
Wolff, et al.: Burger's Medicinal Chemistry and Drug Discovery—Fifth Ed. New York: John Wiley & Sons, 1996; vol. 1, pp. 975-977.
Wong, J. et al. "Distinct Requirements for Chromatin Assembly in Transcriptional Repression by Thyroid Hormone Receptor and Histone Deacetylase." EMBO J., 1998; 17(2):520-534.
Yang, W. M. et al., "Transcriptional repression by YY1 is mediated by interaction with a mammalian homolog of the yeast global regulator RPD3," Proc. Natl. Acad. Sci. U.S.A., Nov. 12, 1996, vol. 93, No. 23, pp. 12845-12850.
Yang, W. M. et al., "Isolation and characterization of cDNAs corresponding to an additional member of the human histone deacetylase gene family," J. Biol. Chem., Oct. 31, 1997, vol. 272, No. 44, pp. 28001-28007.
Yoshida, M. et al. "Trichostatin and Leptomycin: Inhibition of Histone Deacetylation and Signal-Dependent Nuclear Export." Ann. Ny. Y. Acad. Sci., 1999; 886:23-36.
Yoshida, M. et al. "Reversible Arrest of Proliferation of rat 3Y1 Fibroblasts in Both G1 and G2 Phases by Trichostatin A." Exp. Cell. Res., 1988; 177(1): 122-131.
Yoshida, M. et al. "Potent and Specific Inhibition of Mammalian Histone Deacetylase Both in Vivo and in Vitro by Trichostatin A." J. Biol. Chem, 1990; 265(28): 17174-17179.
Yoshida, M. et al. "Structural Specificity for Biological Activity of Trichostatin A, a Specific Inhibitor of Mammalian Cell Cycle with Potent Differentiation-Inducing Activity in Friend Leukemia Cells." J. Antibiot. (Tokyo), 1990; 43(9): 1101-1106.
Zenger, M. et al. "Chapter 27: Structure-Activity Relationship and Drug Design." Remington's Pharmaceutical Sciences, 16th Ed. (1980): pp. 420-425.
Emiliani, s. et al. "Characterization of a Human RPD3 Ortholog, HDAC3." Proc. Natl. Acad. Sci. USA, 1998; 95(6): 2795-2800.
Finnin et al. "Structures of a Histone Deacetylase Homologue Bound to the TSA and SAHA Inhibitors." Nature, 1999; 401(6749): 188-193.
Grozinger et al. "Three Proteins Define a Class of Human Histone Deacetylase Related to Yeast Hdalp." Proc. Natl. Acad. Sci. USA, 1999; 96(9): 4868-4873.
Plumb, J. A. et al., "Epigenetic approaches to cancer therapy," Biochem. Soc. Trans., Dec. 2004, vol. 32, Pt. 6, pp. 1095-1097.
Adler, J.T. et al., "Inhibition of Growth in Medullary Thyroid Cancer Cells with Histone Deacetylase Inhibitors and Lithium Chloride", Journal of Surgical Research, (2010), vol. 159, pp. 640-644.
Aravantinos G. et al., "Phase II study of docetaxel-vinorelbine in platinum-resistant, paclitaxel-pretreated ovarian cancer." Ann. Oncol., Jul. 2003; 14(7): 1094-1099.
Arnold, N.B. et al., "The Histone Deacetylase Inhibitor Suberoylanilide Hydroaxamic Acid Induces Growth Inhibition and Enhances Gemcitabine-Induced Cell Death in Pancreatic Cancer", Clin. Cancer Res., (2007), vol. 13, pp. 18-26.
Banwell, C.M. et al., "Targeting 1alpha,25-dihydroxyvitamin D3 Antiproliferative Insensitivity in Breast Cancer Cells by Co-Treatment with Histone Deacetylation Inhibitors", Journal of Steroid Biochemistry & Molecular Biology, (2004), vol. 89-90, pp. 245-249.
Baradari, V. et al., "Histone Deacetylase Inhibitor MS-275 Alone or Combined with Bortezomib or Sorafenib Exhibits Strong

(56) References Cited

OTHER PUBLICATIONS

Antiproliferative Action in Human Cholangiocarcinoma Cells", World Journal of Gastroenterology, (Sep. 7, 2007), vol. 13, No. 33, pp. 4458-4466.

Wedel, S. et al., "Inhibitory Effects of the HDAC Inhibitor Valproic Acid on Prostrate Cancer Growth Are Enhanced by Simultaneous Application of mTOR Inhibitor RAD001", Life Sciences, (2011), vol. 88, pp. 418-424.

Berenbaum et al., "What is Synergy?" Pharmacological Reviews, Jun. 1989; 41(2): 93-141.

Yang et al. "Knockdown of Rab25 expression by RNAi inhibits growth of human epithelial ovarian cancer cells in vitro and in vivo." Pathology, Dec. 2006; 38(6): 561-567.

Bolden, J.E. et al., "Anticancer activites of histone deacetylase inhibitors," Nat. Rev. Drug Discov., Sep. 2006, vol. 5, No. 9, pp. 769-784.

Bookman, M. A. et al., "Extending the platinum-free interval in recurrent ovarian cancer: the role of topotecan in second-line chemotherapy," Oncologist, 1999, vol. 4, No. 2, pp. 87-94.

Zhao, J.-Y. et al., "SAHA and Curcumin Combinations Co-Enhance Histone Acetylation in Human Cancer Cells But Operate Antagonistically in Exerting Cytotoxic Effects", Journal of Asian Natural Products Research, (May 2010), vol. 12, No. 5, pp. 335-348.

"Guidance for Industry: S1C(R2) Dose selection for carcinogenicity studies," U.S. Department of Health and Human Services, Food and Drug Administration, Center for Drug Evaluation and Research (CDER), Center for Biologics Evaluation and Research (CBER), Sep. 2008.

Chou T. C. "Theoretical basis, experimental design, and computerized simulation of synergism and antagonism in drug combination studies." Pharmacol. Rev. Sep. 2006; 58(3): 621-81.

Dalgard, C.L. et al., "Evaluation of the In vitro and In vivo Antitumor Activity of Histone Deacetylase Inhibitors for the Therapy of Retinoblastoma", Clinical Cancer Research, (2008), vol. 14, pp. 3113-3123.

De Los Santos, M. et al., "Anti-estrogenic Actions of Histone Deacetylase Inhibitors in MCF-7 Breast Cancer Cells", Endocrine-Related Cancer, (2007), vol. 14, pp. 1021-1028.

De Ruijter, A.J.M. et al., "Antagonistic Effects of Sequential Administration of BL1521, a Histone Deacetylase Inhibitor, and Gemcitabine to Neuroblastoma Cells", Cancer Letters, (2006), vol. 233, No. 2, pp. 240-246.

Dörwald et al., "Side reactions in organic synthesis: A guide to successful synthesis design," Weinheim: Wiley-VCH Verlag GmbH & Co. KgaA, 2005, Preface.

Entin-Meer, M. et al., "AN-113, a Novel Prodrug of 4-Phenylbutyrate with Increased Anti-neoplastic Activity in Glioma Cell Lines", (2007), vol. 253, pp. 205-214.

Bouchain, G. et al., "Development of potential antitumor agents, synthesis and biological evaluation of a new set of sulphonamide derivatives as histone deacetylase inhibitors." J. Med. Chem., Jan. 2003; 46(5):820-830.

Andrews et al. "Anti-malarial Effect of Histone Deacetylation Inhibitors and Mammalian Tumour Cytodifferentiating Agents." Int. J. Parasitol., 2000; 30(6): 761-768.

Hamilton T. C. et al., "Characterization of a human ovarian carcinoma cell line (NIH:OVCAR-3) with androgen and estrogen receptors." Cancer Res. Nov. 1983; 43(11): 5379-89.

Havrilesky, L.J. et al. "Weekly low-dose carboplatin and paclitaxel in the treatment of recurrent ovarian and peritoneal cancer." Gynecological Cancer; May 2003; 88(1): 51-57.

Hurtubise, A. et al., "Effect of Histone Deacetylase Inhibitor LAQ824 on Antineoplastic Action of 5-Aza-2'-deoxycytidine (Decitabine) on Human Breast Carcinoma Cells", Cancer Chemother. Pharmacol., (2006), vol. 58, pp. 618-625.

Jang, E.-R. et al., "Different Effect of Protein Kinase B/Akt and Extrcellular Signal-Regulated Kinase Inhibition on Trichostatin A—Induced Apoptosis in Epithelial Ovarian Carcinoma Cell Lines", Mol. Cell Biochem., (2011), vol. 353, pp. 1-11.

Bernhard, D. et al. "Apoptosis Induced by the Histone Deacetylase Inhibitor Sodium Butyrate in Human Leukemic Lymphoblasts." FASEB J., 1999; 13(14): 1991-2001.

Jordan, V.C. "Tamoxifen: A Most Unlikely Pioneering Medicine." Nat Rev Drug Discov., Mar. 2003; 2(3): 205-213.

Kano, Y. et al., "Cytotoxic Effects of Histone Deacetylase Inhibitor FK228 (Depsipeptide, formerly named FR901228) in Combination with Conventional Anti-Leukemia/Lymphoma Agents Against Human Leukemia/Lymphoma Cell Lines", Invest. New Drugs, (2006), vol. 25, pp. 31-40.

Khan, S.B. et al., "Analysis of Histone Deacetylase Inhibitor, Depsipeptide (FR901228), Effect on Multiple Myeloma", British Journal of Haematology, (2004), vol. 125, pp. 156-161.

Kim, J.C. et al., "In Vitro Evaluation of Histone Deacetylase Inhibitors as Combination Agents for Colorectal Cancer", Anticancer Research, (2009), vol. 29, pp. 3027-3034.

Bernstein, B. E. et al., Genomewide studies of histone deacetylase function in yeast. Proc Natl Acad Sci U S A. Dec. 5, 2000, vol. 97, No. 25, pp. 13708-13713. Erratum in: Proc Natl Acad Sci U S A Apr. 24, 2001, vol. 98, No. 9, pp. 5368.

Kuzuya K. et al., "Optimal doses of paclitaxel and carboplatin combination chemotherapy for ovarian cancer: a phase I modified continual reassessment method study." Int. J. Clin. Oncol. Dec. 2001; 6(6): 271-8.

Lai, J.-P. et al., "Additive Effective of Apicidin and Doxorubicin in Sulfatase 1 Expressing Hepatocellular Carcinoma In Vitro and In vivo", Journal of Hepatology, vol. 50, pp. 1112-1121.

Li, P. et al., "Coordination of PAD4 and HDAC2 in the Regulation of p53-Target Gene Expression", (2010), vol. 29, pp. 3153-3162.

Brehm, A. et al., "Retinoblastoma protein recruits histone deacetylase to repress transcription," Nature, Feb. 5, 1998, vol. 391, No. 6667, pp. 597-601.

Neijt, J.P. et al. "Paclitaxel/carboplatin for the initial treatment of advanced ovarian cancer." Seminars in Oncology, Feb. 1999; 26(2 Suppl.): 78-83.

Ozols, R.F. "Recurrent Ovarian Cancer: Evidence-based Treatment." J. Clin. Oncol., Mar. 2002; 20(5): 1161-1163.

Paris M. et al., "Histone deacetylase inhibitors: from bench to clinic." J Med Chem. Mar. 27, 2008; 51(6):1505-29. Epub Feb. 5, 2008.

Chang et al. "Activation of the BRLF1 Promoter and Lytic Cycle of Epstein-Barr Virus by Histone Acetylation." Nucleic Acids Res., 2000; 28(20):3918-3925.

Peng, C.-Y. et al., "Growth-Inhibiting Effects of Arsenic Trioxide Plus Epigenetic Therapeutic Agents on Leukemia Cell Lines", Leukemia & Lymphoma, (Feb. 2010), vol. 51, No. 2, pp. 297-303.

Dangond et al. "Differential Display Cloning of a Novel Human Histone Deacetylase (HDAC3) cDNA from PHA-Activated Immune Cells." Biochem. Biophys. Res. Commun., 1998; 242(3): 648-652.

Plumb, J.A. et al. "Pharmacodynamic Response and Inhibition of Growth of Human Tumor Xenografts by the Novel Histone Deacetylase inhibitor PXD101." Mol. Cancer Ther., Aug. 2003; 2: 721-728.

David, G. et al. "Histone Deacetylase Associated with mSin3A Mediates Repression by the Acute Promyelocytic Leukemia-associated PLZF Protein." Oncogene, 1998; 16(19): 2549-2556.

Rovida, E. et al., "The c-Jun-N-terminal-Kinase Inhibitor SP600125 Enhances the Butyrate Derivative D1-Induced Apoptosis Via Caspase 8 Activation in Kasumi 1 t(8;21) Acute Myeloid Leukaemia Cells", British Journal of Haematology, (2006), vol. 135, pp. 653-659.

Davie, J. R., "Covalent modifications of histones: expression from chromatin templates," Curr. Opin. Genet. Dev., Apr. 1998, vol. 8, No. 2, pp. 173-178.

Sonnemann, J. et al., "Comparative Evaluation of the Treatment Efficacy of Suberoylanilide Hydroxamic Acid (SAHA) and Paclitaxel in Ovarian Cancer Cell Lines and Primary Ovarian Cancer Cells from Patients", BMC Cancer, (2006), vol. 6, pp. 183.

Taddei, A. et al., "The Effects of Histone Deacetylase Inhibitors on Heterochromatin: Implications for Anticancer Therapy", EMBO Reports, (2005), vol. 6, No. 6, pp. 520-524.

Thigpen J. T. et al., Second-line chemotherapy for recurrent carcinoma of the ovary. Cancer. Feb. 15, 1993; 71(4 Suppl):1559-64.

(56) References Cited

OTHER PUBLICATIONS

Touma, S.E. et al., "Retinoic Acid and the Histone Deacetylase Inhibitor Trichostatin A Inhibit the Proliferation of Human Renal Cell Carcinoma in a Xenograft Tumor Model", Clinical Cancer Research, (2005), vol. 11, pp. 3558-3566.

Vasey, P. et al. "Phase III Randomized Trial of Docetaxel-Carboplatin Versus Paclitaxel-Carboplatin as First-line Chemotherapy for Ovarian Carcinoma." J. Natl. Cancer Inst., Nov. 2004; 96(22): 1682-1691.

Vippagunta, S. R. et al., "Crystalline solids," Adv. Drug Deliv. Rev., May 16, 2001, vol. 48, No. 1, pp. 3-26, pp. 18.

Moore, P.S. et al., "Gene expression profiling after treatment with the histone deacetylase inhibitor trichostatin A reveals altered expression of both pro-and anti-apoptotic genes in pancreatic adenocarcinoma cells," Biochim. Biophys. Acta., Sep. 17, 2004, vol. 1693, No. 3, pp. 167-176.

Stapnes, C. et al., "Functional characteristics and gene expression profiles of primary acute myeloid leukaemia cells identify patient subgroups that differ in susceptibility to histone deacetylase inhibitors," Int. J. Oncol., Dec. 2007, vol. 31, No. 6, pp. 1529-1538.

Yamagishi, S. et al., "Expression of dihydropyrimidine dehydrogenase, thymidylate synthase, p53 and p21 in metastatic liver tumor from colorectal cancer after 5-fluorouracil-based chemotherapy," Anticancer Res., Mar.-Apr. 2005, vol. 25, No. 2B, pp. 1237-1242.

Lee, J.H. et al. "Histone deacetylase inhibitor enhances 5-fluorouracil cytotoxicity by down-regulating thymidylate synthase in human cancer cells." Mol. Cancer Ther., Dec. 2006; 5(12): 3085-3095.

Gimsing, P. et al., A phase I clinical trial of the histone deacetylase inhibitor belinostat in patients with advanced hermatological neoplasia. Eur J Haematol. Sep. 2008, vol. 81, No. 3, pp. 170-176.

Steele, N. L. et al., A phase 1 pharmacokinetic and pharmacodynamic study of the histone daecetylase inhibitor belinostat in patients with advanced solid tumors. Clin. Cancer Res. Feb. 1, 2008, vol. 14, No. 3, pp. 804-810.

Advani, R. et al., 2007, "Belinostat (PXD101) in patients with recurrent or refractory peripheral or cutaneous T-cell lymphoma: results of a phase II study," American Society for Hematology, vol. 110, Abstract No. 3453.

Avis, K.E. et al. (editors), 1992, "Pharmaceutical Dosage Forms: parenteral medications," second edition, pp. 514-518.

Gimseng et al., 2005, "Activity of the histone deacetylase (HDAC) inhibitor PXD101 in preclinical studies and in a phase I study in patients with advanced hematological tumors," American Society of Hematology, vol. 106, Abstract No. 3337.

Gimseng, P. et al., 2009, "Belinostat: a new broad acting antineoplastic histone deacetylase inhibitor," Expert Opin. Investig, Drugs, vol. 18, pp. 501-508.

Mackay, H. J. et al., 2007, "A phase II trial of the histone deacetylase inhibitor belinostat (PXD101) in patients with platinum resistant epithelial ovarian tumors and micropapillary/borderline (LMP) ovarian tumors. A trial of the PMH phase II consortium," AACR-NCI-EORTC Annual Meeting 2007, American Association for Cancer Research: Molecular Targets and Cancer Therapeutics.

Sinha et al., 2007, "A phase I/II study of the safety and anticancer activity of IV-administered belinostat (PXD101) plus carboplatin (C) or paclitaxel (P), or both in patients with advanced solid tumours," 2007 Annual Meeting of the American Society of Clinical Oncology, Abstract No. 3574.

Sullivan, D. et al., 2006, "A Phase II Study of PXD101 in Advanced Multiple Myeloma," 2006, Annual Meeting of the American Society for Hematology, 2006, ASH Annual Meeting Abstracts, Part 1, vol. 108, Abstract 3583.

\* cited by examiner

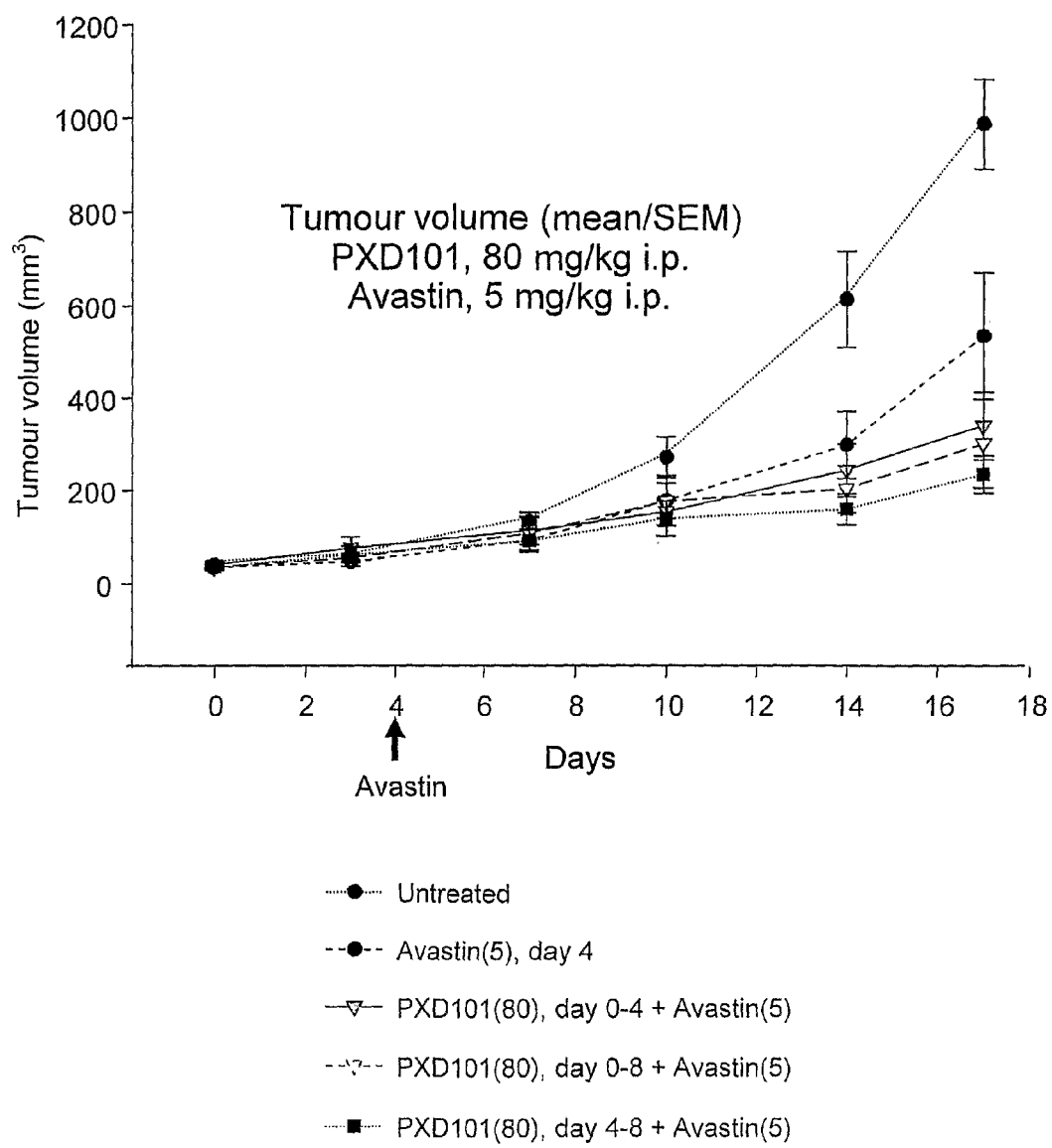

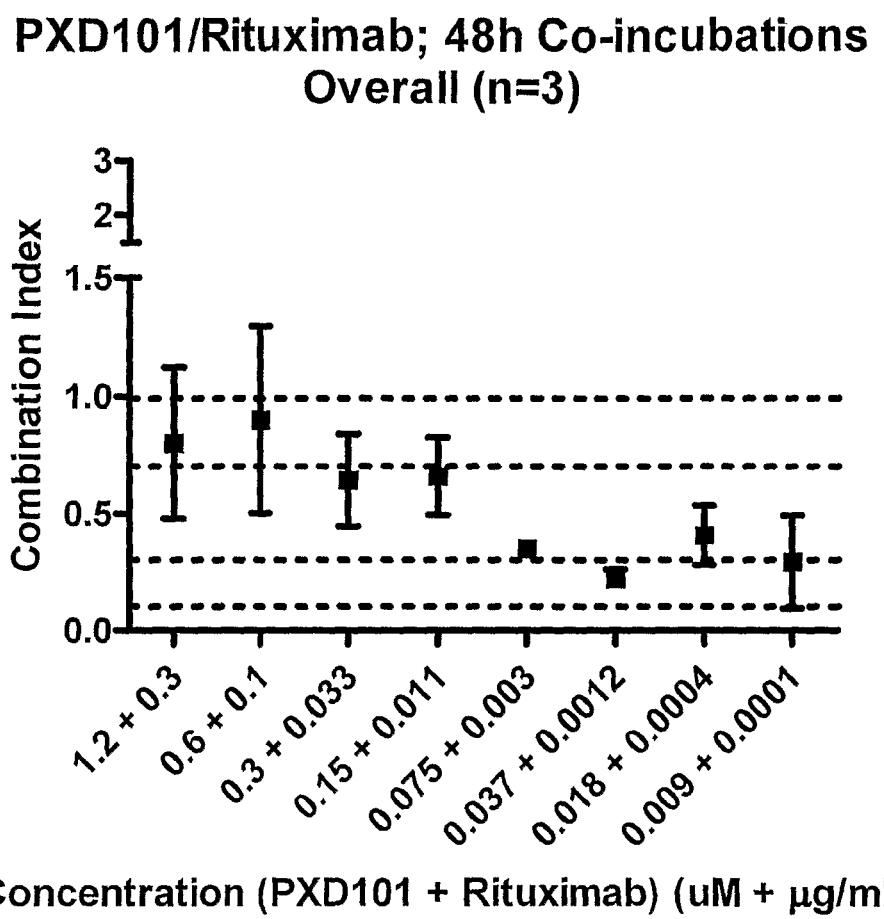

HISTONE DEACETYLASE (HDAC) INHIBITORS (PXD101) FOR THE TREATMENT OF CANCER ALONE OR IN COMBINATION WITH CHEMOTHERAPEUTIC AGENT

RELATED APPLICATION

This application is a national stage filing under 35 U.S.C. 371 of International Application No. PCT/GB2006/004215 filed on 10 Nov. 2006, which is related to U.S. provisional patent application 60/735,701 filed 10 Nov. 2005, the contents of which are incorporated herein by reference in their entireties.

FIELD OF INVENTION

The present invention relates to methods for treating cancer. In one respect, the present invention relates to a method of treating cancer (e.g., solid tumour cancer, e.g., rectal cancer, colon cancer, ovarian cancer; hematological cancer, e.g., multiple myeloma, leukemia, lymphoma) comprising administering to a patient in need thereof, a first amount of a histone deacetylase (HDAC) inhibitor, for example, a histone deacetylase inhibitor as described herein, for example, PXD-101, and a second amount of an other chemotherapeutic agent, for example, an other chemotherapeutic agent selected from: an antibody against VEGF, AVASTIN® (bevacizumab), an antibody against CD20, rituximab, bortezomib, thalidomide, dexamethasone, vincristine, doxorubicin, or melphalan, wherein the first and second amounts together comprise a therapeutically effective amount. In another respect, the present invention relates to a method of treating a hematological cancer (e.g., multiple myeloma, leukemia, lymphoma) comprising administering to a patient in need thereof a therapeutically effective amount of a histone deacetylase inhibitor, for example, a histone deacetylase (HDAC) inhibitor as described herein, for example, PXD-101.

BACKGROUND

A number of patents and publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

As used herein, "a," "an" and "the" include singular and plural referents unless the context clearly dictates otherwise. Thus, for example, reference to "an active agent" or "a pharmacologically active agent" includes a single active agent as well a two or more different active agents in combination, reference to "a carrier" includes mixtures of two or more carriers as well as a single carrier, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

Multiple Myeloma

Multiple myeloma is a disseminated malignancy of plasma cells that affects approximately 14,600 new patients each year in the United States. The etiology of this rare blood disease, affecting mainly the middle-aged to elderly population, is largely unknown although genetic predisposition and environmental factors have been implicated. From onset, malignant plasma cells arising from clonal expansion accumulate in the bone marrow, producing abnormally high levels of immunoglobulins. Multiple myeloma is difficult to diagnose early because there may be no symptoms in early stage. Bone pain especially secondary to compression fractures of the ribs or vertebrae is the most common symptom.

Dexamethasone is a commonly used regimen for first-line treatment of this disease. More recently, combinations of vincristine, doxorubicin, and dexamethasone (VAD) have been used to treat multiple myeloma. However, these are not effective long-term treatments. Dexamethasone treatment has a response rate of approximately 25-35%.

In many patients, high-dose chemotherapy supported by autologous stem cell transplantation (ASCT) may prolong event-free survival if the procedure is performed within 12 months of initial diagnosis. However almost all patients receiving high-dose chemotherapy and an autologous peripheral stem cell transplant will ultimately relapse.

Lymphoma

Despite years of research into the development of new methods of treatment, cancers of the lymphatic system, or lymphomas, remain quite common. For example, more than 60,000 people in the United States are diagnosed with lymphoma each year, including more than 55,000 cases of non-Hodgkin's Lymphoma (NHL), and these numbers are constantly increasing. In addition, the prognosis for those affected by these diseases is often poor, as the survival rates for lymphoma patients remain low. Clearly, new methods for treating these diseases are needed.

While traditional treatments for lymphoma typically depend on the type of lymphoma as well as the medical history of the patient, first-line treatment for many lymphomas typically includes chemotherapy. Such chemotherapy will often entail the administration of a "cocktail" of compounds, e.g., the formulation CHOP, which includes cyclophosphamide, doxorubicin, vincristine, and prednisone. In addition, certain first-line cancer treatments also include other forms of cancer therapy, such as radiation therapy.

In many cases, patients respond initially to such first-line treatments, but subsequently suffer a relapse, i.e., a tumor reappears or resumes growing. Following one such relapse, patients are often treated with further chemotherapy, e.g., with CHOP or with other formulations, or, in some cases, the patients are treated with other procedures such as bone marrow transplantation. Again, in many cases, patients initially respond to such additional treatments, but subsequently suffer another relapse. In general, the more relapses a patient suffers, the less agreement there is in the art concerning optimal subsequent treatment. In other cases, a patient fails to respond at all to a treatment, even initially, and is thus said to have a refractory cancer. In such cases as well, little agreement exists in the art regarding optimal subsequent treatment.

Leukemia

Leukemia is a malignant cancer of the bone marrow and blood. It is characterized by the uncontrolled growth of blood cells. The common types of leukemia are divided into four categories: acute or chronic myelogenous, involving the myeloid elements of the bone marrow (white cells, red cells, megakaryocytes) and acute or chronic lymphocytic, involving the cells of the lymphoid lineage.

Acute leukemia is a rapidly progressing disease that results in the massive accumulation of immature, functionless cells (blasts) in the marrow and blood. The marrow often can no longer produce enough normal red and white blood cells and platelets. Anemia, a deficiency of red cells, develops in virtually all leukemia patients. The lack of normal white cells impairs the body's ability to fight infections. A shortage of platelets results in bruising and easy bleeding. In contrast, chronic leukemia progresses more slowly and leads to unregulated proliferation and hence marked overexpansion of a spectrum of mature (differentiated) cells. In general, acute leukemia, unlike the chronic form, is potentially curable by elimination of the neoplastic clone.

It is estimated that there will be 28,700 new cases of leukemia in the United States this year; about equal proportions are acute leukemia and chronic types. Most cases occur in older adults. In fact, more than half of all cases of leukemia occur in persons over 60. The most common types of leukemia in adults are acute myelogenous leukemia (AML), with an estimated 9,400 new cases annually, chronic lymphocytic leukemia (CLL), with some 7,300 new cases this year, and chronic myeloid leukemia (CML). The most common type of leukemia in children is acute lymphocytic leukemia (ALL).

Standard treatment for leukemia usually involves chemotherapy and/or bone marrow transplantation and/or radiation therapy.

Chemotherapy in leukemia usually involves a combination of two or more anti-cancer drugs. Approximately 40 different drugs are now being used in the treatment of leukemia. Some common combinations include cytarabine with either doxorubicin or daunorubicin or mitoxantrone or thioguanine, mercaptopurine with methotrexate, mitoxantrone with etoposide, asparaginase with vincristine, daunorubicin and prednisone, cyclophosphamide with vincristine, cytarabine and prednisone, cyclophosphamide with vincristine and prednisone, daunorubicin with cytarabine and thioguanine and daunorubicin with vincristine and prednisone.

The two major types of bone marrow transplants are autologous (uses the patient's own marrow) and allogeneic (uses marrow from a compatible donor).

Radiation therapy, which involves the use of high-energy rays, is usually given before bone marrow transplantation to kill all leukemic cells.

Treatment of leukemia is very complex. Tremendous clinical variability among remissions is also observed in leukemic patients, even those that occur after one course of therapy. Patients who are resistant to therapy have very short survival times, regardless of when the resistance occurs. Despite improvements in outcome with current treatment programs, the need to discover novel agents for the treatment of all types of leukemia continues.

Thus, there is an urgent need for improved therapies for the treatment of multiple myeloma. Specifically, there is a need to discover effective single and combination therapies that will improve response rates and/or reduce the relapse rates in the treatment of multiple myeloma, both as first-line treatments and for the treatment of relapsed subjects.

SUMMARY OF THE INVENTION

Combination Therapy in the Treatment of Cancer

The present invention is also based, in part, upon the discovery that histone deacetylase (HDAC) inhibitors, such as PXD-101, have a synergy with other chemotherapeutic agents, when used together in the treatment of cancer.

Accordingly, one aspect of the present invention is a method of treating cancer comprising administering to a patient in need thereof, a first amount of a histone deacetylase (HDAC) inhibitor, for example, a histone deacetylase inhibitor as described herein, for example, PXD-101, and a second amount of an other chemotherapeutic agent, for example, an other chemotherapeutic agent selected from: an antibody against VEGF, AVASTIN® (bevacizumab), an antibody against CD20, rituximab, bortezomib, thalidomide, dexamethasone, vincristine, doxorubicin, and melphalan, wherein the first and second amounts together comprise a therapeutically effective amount.

Another aspect of the present invention is a histone deacetylase (HDAC) inhibitor, for example, a histone deacetylase inhibitor as described herein, for example, PXD-101, for use in a method of treatment of a cancer, wherein said treatment comprises treatment with: (i) said histone deacetylase inhibitor and (ii) an other chemotherapeutic agent, for example, an other chemotherapeutic agent selected from: an antibody against VEGF, AVASTIN® (bevacizumab), an antibody against CD20, rituximab, bortezomib, thalidomide, dexamethasone, vincristine, doxorubicin, and melphalan.

Another aspect of the present invention is use of a histone deacetylase (HDAC) inhibitor, for example, a histone deacetylase inhibitor as described herein, for example, PXD-101, in the manufacture of a medicament for the treatment of cancer, wherein said treatment comprises treatment with: (i) said histone deacetylase inhibitor and (ii) an other chemotherapeutic agent, for example, an other chemotherapeutic agent selected from: an antibody against VEGF, AVASTIN® (bevacizumab), an antibody against CD20, rituximab, bortezomib, thalidomide, dexamethasone, vincristine, doxorubicin, and melphalan.

In one embodiment, the cancer is a solid tumour cancer, e.g., rectal cancer, colon cancer, ovarian cancer. In one embodiment, the cancer is a hematological cancer. In one embodiment, the hematological cancer is multiple myeloma, lymphoma, or leukemia. In one embodiment, the hematological cancer is multiple myeloma. In one embodiment, the hematological cancer is lymphoma, e.g., non-Hodgkin's lymphoma (NHL). In one embodiment, the hematological cancer is leukemia, e.g., myelogenous leukaemia, lymphocytic leukaemia, e.g., acute myelogenous leukaemia (AML), chronic myelogenous leukaemia (CML), acute lymphocytic leukaemia (ALL), chronic lymphocytic leukaemia (CLL).

Another aspect of the present invention is a method (e.g., an in vitro method, an in vivo method) for selectively inducing terminal differentiation, cell growth arrest and/or apoptosis of, or reducing the viability of, a neoplastic cell, e.g., a neoplastic cell characteristic of hematological cancer, e.g., a myeloma cell, a plasmacytoma cell, or a plasma cell leukemia cell, wherein the method comprises contacting the neoplastic cell with a first amount of a histone deacetylase (HDAC) inhibitor, for example, a histone deacetylase inhibitor as described herein, for example, PXD-101, and a second amount of an other chemotherapeutic agent, for example, an other chemotherapeutic agent selected from: an antibody against VEGF, AVASTIN® (bevacizumab), an antibody against CD20, rituximab, bortezomib, thalidomide, dexamethasone, vincristine, doxorubicin, and melphalan, wherein the first and second amounts together comprise an effective amount.

Another aspect of the present invention is a method (e.g., an in vitro method, an in vivo method) of preventing, inhibiting (fully or partially), or arresting cell proliferation of a neoplastic cell, e.g., a neoplastic cell characteristic of hematological cancer, e.g., a myeloma cell, a plasmacytoma cell, or a plasma cell leukemia cell, wherein the method comprises contacting the neoplastic cell with a first amount of a histone deacetylase (HDAC) inhibitor, for example, a histone deacetylase inhibitor as described herein, for example, PXD-101, and a second amount of an other chemotherapeutic agent, for example, an other chemotherapeutic agent selected from: an antibody against VEGF, AVASTIN® (bevacizumab), an antibody against CD20, rituximab, bortezomib, thalidomide, dexamethasone, vincristine, doxorubicin, and melphalan, wherein the first and second amounts together comprise an effective amount.

Treatment of Hematological Cancers

The present invention is based, in part, upon the discovery that histone deacetylase (HDAC) inhibitors, such as PXD-101, can be used to provide therapeutically effective treatments against hematological cancers (e.g., multiple myeloma, leukemia, lymphoma). Specifically, PXD-101 was found to inhibit cell proliferation, migration, reduce viability and/or induce apoptosis in hematological cancer cells.

Accordingly, one aspect of the present invention is a method of treating a hematological cancer comprising administering to a patient in need thereof a therapeutically effective amount of a histone deacetylase (HDAC) inhibitor, for example, a histone deacetylase inhibitor as described herein, for example, PXD-101.

Another aspect of the present invention is a histone deacetylase (HDAC) inhibitor, for example, a histone deacetylase inhibitor as described herein, for example, PXD-101, for use in a method of treatment of a hematological cancer.

Another aspect of the present invention is use of a histone deacetylase (HDAC) inhibitor, for example, a histone deacetylase inhibitor as described herein, for example, PXD-101, in the manufacture of a medicament for the treatment of a hematological cancer.

In one embodiment, the hematological cancer is multiple myeloma, lymphoma, or leukemia. In one embodiment, the hematological cancer is multiple myeloma. In one embodiment, the hematological cancer is lymphoma, e.g., non-Hodgkin's lymphoma (NHL). In one embodiment, the hematological cancer is leukemia, e.g., myelogenous leukaemia, lymphocytic leukaemia, e.g., acute myelogenous leukaemia (AML), chronic myelogenous leukaemia (CML), acute lymphocytic leukaemia (ALL), chronic lymphocytic leukaemia (CLL).

Another aspect of the present invention is a method (e.g., an in vitro method, an in vivo method) for selectively inducing terminal differentiation, cell growth arrest and/or apoptosis of, or reducing the viability of, a neoplastic cell characteristic of hematological cancer, e.g., a myeloma cell, a plasmacytoma cell, or a plasma cell leukemia cell, wherein the method comprises contacting the neoplastic cell with an effective amount of a histone deacetylase (HDAC) inhibitor, for example, a histone deacetylase inhibitor as described herein, for example, PXD-101.

Another aspect of the present invention is a method (e.g., an in vitro method, an in vivo method) of preventing, inhibiting (fully or partially), or arresting cell proliferation of a neoplastic cell characteristic of hematological cancer, e.g., a myeloma cell, a plasmacytoma cell, or a plasma cell leukemia cell, wherein the method comprises contacting the neoplastic cell with an effective amount of a histone deacetylase (HDAC) inhibitor, for example, a histone deacetylase inhibitor as described herein, for example, PXD-101.

BRIEF DESCRIPTION OF THE DRAWINGS

FIG. 4 depicts the in vivo synergy of PXD-101 with Avastin® in mouse xenografts of the ovarian tumour cell line A2780.

FIG. 5 depicts a graph showing the synergy of PXD-101 with rituximab in the cell line SU-DHL-4. Synergy of PXD-101 with rituximab was also seen in the lymphoma lines Ramos and Raji (data not shown).

DETAILED DESCRIPTION OF THE INVENTION

Figure 1:
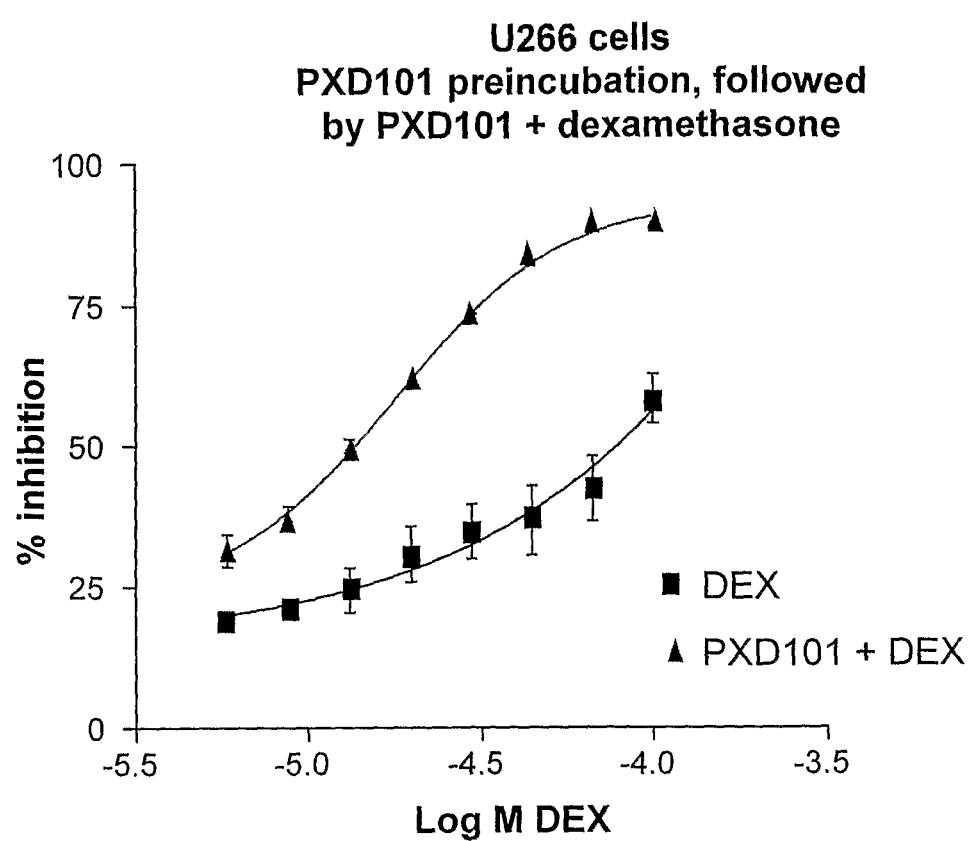
FIG. 1 depicts a graph demonstrating the results of a combination study of the effects of PXD-101 and dexamethasone on a myeloma cell line (i.e., U266).

Solely for clarity of disclosure, and not by way of limitation, the Detailed Description of the present invention is divided into the following subsections:
I. Histone Deacetylases and Histone Deacetylase Inhibitors.
II. Chemotherapeutic Agents.
III. Therapeutic-Uses.
IV. Modes and Doses of Administration.
V. Pharmaceutical Compositions.

I. Histone Deacetylases and Histone Deacetylase Inhibitors

Histone deacetylases are involved in the reversible acetylation of histone and non-histone proteins (p53, tubulin, and various transcription factors). Mammalian HDACs have been ordered into three classes based upon their similarity to known yeast factors. Class I HDACs (HDACs 1, 2, 3 and 8) bear similarity to the yeast RPD3 protein, are located in the nucleus and are found in complexes associated with transcriptional co-repressors. Class II HDACs (HDACs 4, 5, 6, 7 and 9) are similar to the yeast HDA1 protein, and have both nuclear and cytoplasmic subcellular localization. Class III HDACs form a structurally distant class of NAD dependent enzymes that are related to the yeast SIR2 proteins.

Compounds that are shown to inhibit HDAC activity fall into five structurally diverse classes: (1) hydroxamic acids; (2) cyclic tetrapeptides; (3) aliphatic acids; (4) benzamides; and (5) electrophilic ketones.

Hydroxamic acids were among the first HDAC inhibitors identified and these agents helped define the model pharmacophore for HDAC inhibitors. The linker domain of these agents is comprised of linear or cyclic structures, either saturated or unsaturated, and the surface recognition domain is generally a hydrophobic group, most often aromatic. Phase I and II clinical trials are currently on-going for several hydroxamic acid based HDAC inhibitors, including PXD-101.

PXD-101 is a highly potent HDAC inhibitor that blocks proliferation of diverse tumor cell lines at low micromolar potency ($IC_{50}$ 0.08-2.43 µM) and HDAC enzyme activity ($IC_{50}$ 9-110 nM). In xenograft models, PXD-101 slows tumor growth. In addition, PXD-101 causes cell cycle arrest and apoptosis in rapidly proliferating cells.

Hydroxamic acid based HDAC inhibitors are particularly suitable for use in the present invention.

In one embodiment, the HDAC inhibitor used in the present invention is selected from compounds of the following formula and pharmaceutically acceptable salts and solvates thereof:

$$A-Q^1-J-Q^2-\overset{O}{\underset{}{C}}-\underset{H}{N}-OH$$

wherein:
A is an unsubstituted phenyl group;
Q$^1$ is a covalent bond, a C$_{1-7}$alkylene group, or a C$_{2-7}$alkenylene group;
J is:

[structure: -N(R$^1$)-S(=O)$_2$-]

R$^1$ is hydrogen, C$_{1-7}$alkyl, C$_{3-20}$heterocyclyl, C$_{5-20}$aryl, or C$_{5-20}$aryl-C$_{1-7}$alkyl; and,
Q$^2$ is:

[structure: para-phenyl-vinyl]  or

[structure: meta-phenyl-vinyl]

In one embodiment, Q$^1$ is a covalent bond, a C$_{1-4}$alkylene group, or a C$_{2-4}$alkenylene group.
In one embodiment, Q$^1$ is a covalent bond.
In one embodiment, Q$^1$ is a C$_{1-7}$alkylene group.
In one embodiment, Q$^1$ is —CH$_2$—, —C(CH$_3$)—, —CH$_2$CH$_2$—, —CH$_2$CH(CH$_3$)—, —CH$_2$CH(CH$_2$CH$_3$)—, —CH$_2$CH$_2$CH$_2$—, or —CH$_2$CH$_2$CH$_2$CH$_2$—.
In one embodiment, Q$^1$ is a C$_{2-7}$alkenylene group.
In one embodiment, Q$^1$ is —CH=CH— or —CH=CH—CH$_2$—.
In one embodiment, R$^1$ is hydrogen or C$_{1-7}$alkyl.
In one embodiment, R$^1$ is hydrogen or C$_{1-3}$alkyl.
In one embodiment, R$^1$ is hydrogen, -Me, -Et, -nPr, -iPr, -nBu, -iBu, -sBu, or -tBu.
In one embodiment, R$^1$ is hydrogen, -Me, or -Et.
In one embodiment, R$^1$ is hydrogen.
In one embodiment, Q$^2$ is:

[structure: para-phenyl-vinyl]

In one embodiment, Q$^2$ is:

[structure: meta-phenyl-vinyl]

All compatible combinations of the above embodiments are disclosed herein, as if each particular combination was individually and explicitly recited.

In one embodiment, the HDAC inhibitor used in the present invention is selected from the following compounds, and pharmaceutically acceptable salts or solvates thereof:

[structure of compound 1: phenyl-N(Me)-SO$_2$-(m-phenyl)-CH=CH-C(=O)-NH-OH]

[structure of compound 2: benzyl-NH-SO$_2$-(m-phenyl)-CH=CH-C(=O)-NH-OH]

[structure of compound 3: phenethyl-NH-SO$_2$-(m-phenyl)-CH=CH-C(=O)-NH-OH]

[structure of compound 4: styryl-SO$_2$-NH-(m-phenyl)-CH=CH-C(=O)-NH-OH]

[structure of compound 5: diphenyl-N-SO$_2$-(m-phenyl)-CH=CH-C(=O)-NH-OH]

[structure of compound 6: phenyl-N(iBu)-SO$_2$-(m-phenyl)-CH=CH-C(=O)-NH-OH]

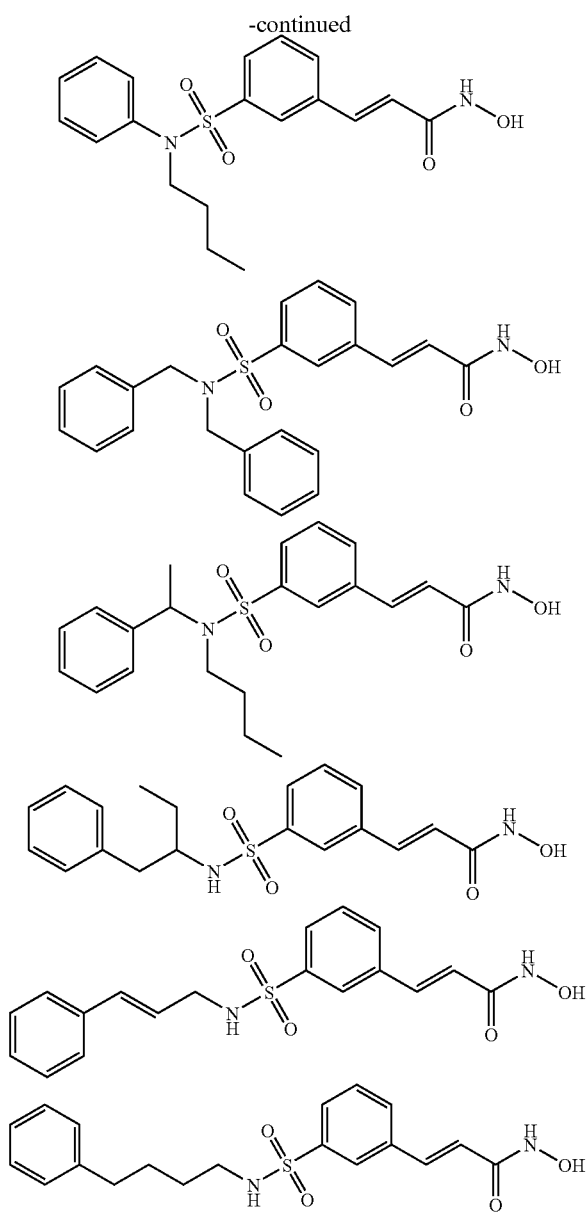

In one embodiment, the HDAC inhibitor used in the present invention is selected from the following compound (also known as PXD-101) and pharmaceutically acceptable salts and solvates thereof:

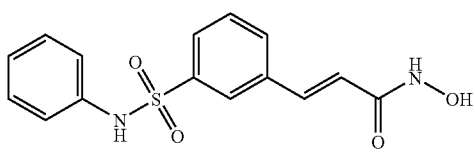 [SMILES: O=C(/C=C/c1cccc(S(=O)(=O)Nc2ccccc2)c1)NO]

Other HDAC inhibitors that are suitable for use in the present invention include the compounds disclosed in U.S. Ser. Nos. 10/381,790; 10/381,794; 10/381,791, which are hereby incorporated by reference in their entirety.

Stereoisomers

Stereoisomers of the above identified compounds within the scope of the present invention. Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the formulas of the invention, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

When an HDAC inhibitor used in the present invention contains one chiral center, the compound exists in two enantiomeric forms, and in such cases, references to the compound herein relates to both enantiomers and mixtures of enantiomers, such as the specific 50:50 mixture referred to as a racemic mixture. The enantiomers can be resolved by methods known to those skilled in the art, for example by formation of diastereoisomer salts which can be separated, for example, by crystallization (see, e.g., CRC Handbook of Optical Resolutions via Diastereomeric Salt Formation by David Kozma (CRC Press, 2001)); by formation of diastereoisomer derivatives or complexes which can be separated, for example, by crystallization, gas-liquid or liquid chromatography; by selective reaction of one enantiomer with an enantiomer-specific reagent, for example enzymatic esterification; or by gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers can be synthesized by asymmetric synthesis using optically active reagents, substrates, catalysts or solvents, or by converting one enantiomer into the other by asymmetric transformation.

Designation of a specific absolute configuration at a chiral carbon is understood to mean that the designated enantiomeric form of the compounds is in enantiomeric excess (ee) or in other words is substantially free from the other enantiomer. For example, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. Enantiomeric excess, as used herein, is the presence of a particular enantiomer at greater than 50%.

For example, the enantiomeric excess can be about 60% or more, such as about 70% or more, for example about 80% or more, such as about 90% or more. In a particular embodiment when a specific absolute configuration is designated, the enantiomeric excess of depicted compounds is at least about 90%. In a more particular embodiment, the enantiomeric excess of the compounds is at least about 95%, such as at least about 97.5%, for example, at least 99% enantiomeric excess.

When an HDAC inhibitor used in the present invention contains two or more chiral carbons it can have more than two optical isomers and can exist in diastereoisomeric forms, and in such cases, references to the compound herein relates to each diastereoisomer of such compounds and mixtures thereof. For example, when there are two chiral carbons, the compound can have up to 4 optical isomers and 2 pairs of enantiomers ((S,S)/(R,R) and (R,S)/(S,R)). The pairs of enantiomers (e.g., (S,S)/(R,R)) are mirror image stereoisomers of one another. The stereoisomers which are not mirror-images (e.g., (S,S) and (R,S)) are diastereomers. The diastereoisomer pairs can be separated by methods known to those skilled in the art, for example chromatography or crystallization and the individual enantiomers within each pair can be separated as described above.

Salts and Solvates

The active compounds disclosed herein can, as noted above, be prepared in the form of their pharmaceutically acceptable salts. Pharmaceutically acceptable salts are salts that retain the desired biological activity of the parent compound and do not impart undesired toxicological effects. Examples of pharmaceutically acceptable salts are discussed in Berge et al., 1977, "Pharmaceutically Acceptable Salts," J. Pharm. Sci., Vol. 66, pp. 1-19. The active compounds disclosed can, as noted above, be prepared in the form of their solvates. The term "solvate" is used herein in the conventional sense to refer to a complex of solute (e.g., active compound, salt of active compound) and solvent. If the solvent is water, the solvate may be conveniently referred to as a hydrate, for example, a hemihydrate, monohydrate, dihydrate, trihydrate, tetrahydrate, and the like.

Prodrugs

Pro-drugs of the HDAC inhibitors disclosed herein are also suitable for use in the present invention. A prodrug of any of the compounds can be made using well known pharmacological techniques.

Isomers, Homologs, and Analogs

Isomers, homologs and analogs of the HDAC inhibitors disclosed herein are also suitable for use in the present invention. In this context, homologs are molecules having substantial structural similarities to the above-described compounds; analogs are molecules having substantial biological similarities regardless of structural similarities; and isomers are compounds that have the same molecular formula, but different structures (e.g., meta, para, or ortho configurations).

II. Chemotherapeutic Agents

The other chemotherapeutic agents that are suitable for use in the present invention (i.e., as the other chemotherapeutic agent used in conjunction with the HDAC inhibitor) include other anti-tumor substances, for example those selected from, for example:

mitotic inhibitors, for example vinblastine;
    alkylating agents, for example cisplatin, carboplatin and cyclophosphamide;
    inhibitors of microtubule assembly, like paclitaxel or other taxanes;
    antimetabolites, for example 5-fluorouracil, capecitabine, cytosine arabinoside and hydroxyurea, or, for example, intercalating antibiotics, for example adriamycin and bleomycin;
    immunomodulators, such as lenalidomide (CC-5013/REVLIMID™ (lenalidomide));
    immunostimulants, for example trastuzumab;
    DNA synthesis inhibitors, e.g. gemcitabine;
    enzymes, for example asparaginase;
    topoisomerase inhibitors, for example etoposide;
    proteasome inhibitors, such as bortezomib;
    biological response modifiers, for example interferon;
    corticosteroids, such as dexamethasone and anti-hormones, for example antioestrogens such as tamoxifen and antiandrogens such as (4'-cyano-3-(4-fluorophenyl-sulphonyl)-2-hydroxy-2-methyl-3'-(trifluoromethyl)-propionanilide;
    antibodies, for example, AVASTIN® (bevacizumab) and rituximab;
    or other therapeutic agents and principles as described in, for example, DeVita, V. T., Jr., Hellmann, S., Rosenberg, S. A.; In: Cancer: Principles & Practice of Oncology, δ.sup.th ed., Lippincott-Raven Publishers (1997).

AVASTIN® (bevacizumab) is a recombinant humanized antibody to Vascular Endothelial Growth Factor (VEGF). AVASTIN® (bevacizumab) is designed to bind to and inhibit VEGF, a protein that plays a critical role in tumor angiogenesis (the formation of new blood vessels to the tumor). Other therapeutic antibodies against VEGF are known in the art including ranibizumab, 2C3 and analogues described in U.S. Pat. No. 6,342,219, and VEGF antibodies described in patent applications EP 0 787 742 and WO 2006/012688.

Rituximab is a monoclonal antibody raised against CD20 which is found on the surface of several cell types including B-cells. Rituximab is therefore indicated for B-cell lymphomas where the antibody adheres to B-cells which are removed by the cells of the immune system. Other antibodies raised against CD20 are known in the art, including tositumomab (Bexxar® BEXXAR® (tositumomab)), ibritumomab, ocrelizumab, ofatumumab, GA-101, SGU-35, TRU-015, Lymphomun, CD20 ValidTarget antibody, and antibodies described in the patent applications WO 2005/000901 and WO 2006/064121.

Methods for preparing and identifying suitable antibodies, for example, an antibody against VEGF, an antibody against CD20, are well known to those of skill in the art.

In one embodiment, the other chemotherapeutic agent is selected from: an antibody against VEGF, AVASTIN® (bevacizumab), an antibody against CD20, rituximab, bortezomib, thalidomide, dexamethasone, vincristine, doxorubicin, and melphalan (also known as L-PAM and PAM)).

In one embodiment, the other chemotherapeutic agent is selected from: an antibody against $VEGF_1$ AVASTIN® (bevacizumab), an antibody against CD20, rituximab, bortezomib, and thalidomide.

In one embodiment, the other chemotherapeutic agent is selected from: an antibody against VEGF, AVASTIN® (bevacizumab), an antibody against CD20, and rituximab.

In one embodiment, the other chemotherapeutic agent is selected from: an antibody against VEGF and AVASTIN® (bevacizumab).

In one embodiment, the other chemotherapeutic agent is selected from: an antibody against CD20 and rituximab.

In one embodiment, the other chemotherapeutic agent is an antibody against VEGF.

In one embodiment, the other chemotherapeutic agent is AVASTIN® (bevacizumab).

In one embodiment, the other chemotherapeutic agent is an antibody against CD20.

In one embodiment, the other chemotherapeutic agent is rituximab.

In one embodiment, the other chemotherapeutic agent is bortezomib.

In one embodiment, the other chemotherapeutic agent is thalidomide.

In one embodiment, the other chemotherapeutic agent is dexamethasone.

In one embodiment, the other chemotherapeutic agent is vincristine.

In one embodiment, the other chemotherapeutic agent is doxorubicin.

In one embodiment, the other chemotherapeutic agent is melphalan.

Of course, although the combination therapy methods described herein require the use of an HDAC inhibitor (e.g., PXD-101) and at least one other chemotherapeutic agent, these combination methods may employ additional chemotherapeutic agents, for example, additional chemotherapeutic agents, for example, additional chemotherapeutic agents as described herein, for example, one or more additional chemotherapeutic agents selected from: an antibody against VEGF, AVASTIN® (bevacizumab), an antibody against CD20, rituximab, bortezomib, thalidomide, dexamethasone, vincristine, doxorubicin, and melphalan.

For example, in one embodiment, the combination therapy method employs an HDAC inhibitor (e.g., PXD-101) and dexamethasone, bortezomib, and doxorubicin.

For example, in one embodiment, the combination therapy method employs an HDAC inhibitor (e.g., PXD-101) and dexamethasone and thalidomide.

III. Therapeutic Uses

The present invention relates to methods for the treatment of cancer.

As used herein, the term "cancer" refers to tumors, neoplasms, carcinomas, sarcomas, leukemias, lymphomas, and the like. For example, cancers include, but are not limited to, leukemias and lymphomas such as cutaneous T-cell lymphoma (CTCL), noncutaneous peripheral T-cell lymphoma, lymphomas associated with human T-cell lymphotropic virus (HTLV), for example, adult T-cell leukemia/lymphoma (ATLL), acute lymphocytic leukemia, acute nonlymphocytic leukemias, chronic lymphocytic leukemia, chronic myelogenous leukemia, Hodgkin's Disease, non-Hodgkin's lymphomas, and multiple myeloma, childhood solid tumors such as brain tumors, neuroblastoma, retinoblastoma, Wilms' Tumor, bone tumors, and soft-tissue sarcomas, common solid tumors of adults such as head and neck cancers (e.g., oral, laryngeal and esophageal), genitourinary cancers (e.g., prostate, bladder, renal, uterine, ovarian, testicular, rectal and colon), lung cancer, breast cancer, pancreatic cancer, melanoma and other skin cancers, stomach cancer, brain cancer, liver cancer, thyroid cancer, and thymoma cancer (including epithelial mediastinal thymoma).

In one embodiment, the cancer to be treated is a solid tumour cancer.

In one embodiment, the cancer to be treated is rectal cancer or colon cancer.

In one embodiment, the cancer to be treated is colon cancer.

In one embodiment, the cancer to be treated is ovarian cancer.

In one embodiment, the cancer to be treated is a hematological cancer.

In one embodiment, the cancer to be treated is multiple myeloma, lymphoma, or leukemia.

In one embodiment, the cancer to be treated is multiple myeloma.

In one embodiment, the cancer to be treated is lymphoma.

In one embodiment, the cancer to be treated is non-Hodgkin's lymphoma (NHL).

In one embodiment, the cancer to be treated is leukemia.

In one embodiment, the cancer to be treated is myelogenous leukaemia.

In one embodiment, the cancer to be treated is lymphocytic leukaemia.

In one embodiment, the cancer to be treated is acute myelogenous leukaemia (AML).

In one embodiment, the cancer to be treated is chronic myelogenous leukaemia (CML).

In one embodiment, the cancer to be treated is acute lymphocytic leukaemia (ALL).

In one embodiment, the cancer to be treated is chronic lymphocytic leukaemia (CLL).

The terms "treatment of cancer" and "cancer treatment", as used herein, refers to partially or totally inhibiting, delaying, or preventing the progression of cancer including cancer metastasis; inhibiting, delaying or preventing the recurrence of cancer including cancer metastasis; or preventing the onset or development of cancer (chemoprevention) in a mammal, for example a human.

The terms "subject" and "patient", as used herein, refer to the recipient of the treatment. Mammalian and non-mammalian subjects are included. In one embodiment, the subject is a mammal, such as a human, canine, murine, feline, bovine, ovine, swine, or caprine. In one preferred embodiment, the subject is a human.

In the context of the methods of treatment described herein which refer to two active agents (e.g., an HDAC inhibitor, e.g., PXD-101 and another chemotherapeutic agent, as described herein), the term "therapeutically effective amount" is intended to qualify the combined amount of the first and second agents in the combination therapy. The combined amount will achieve the desired biological response, for example, partial or total inhibition, delay or prevention of the progression of cancer including cancer metastasis; inhibition, delay or prevention of the recurrence of cancer including cancer metastasis; or the prevention of the onset or development of cancer (chemoprevention) in a mammal, for example a human.

In the context of the methods of treatment described herein which refer to a single active agent (e.g., an HDAC inhibitor, e.g., PXD-101), the term "therapeutically effective amount" is intended to qualify the amount of that agent used in therapy. The amount will achieve the desired biological response, for example, partial or total inhibition, delay or prevention of the progression of cancer including cancer metastasis; inhibition, delay or prevention of the recurrence of cancer including cancer metastasis; or the prevention of the onset or development of cancer (chemoprevention) in a mammal, for example a human.

HDAC Inhibitor Therapy

As discussed above, one aspect of the present invention is a method of treating a hematological cancer comprising administering to a patient in need thereof a therapeutically effective amount of a histone deacetylase (HDAC) inhibitor, for example, a histone deacetylase inhibitor as described herein, for example, PXD-101.

Another aspect of the present invention is a histone deacetylase (HDAC) inhibitor, for example, a histone deacetylase inhibitor as described herein, for example, PXD-101, for use in a method of treatment of a hematological cancer.

Another aspect of the present invention is use of a histone deacetylase (HDAC) inhibitor, for example, a histone deacetylase inhibitor as described herein, for example, PXD-101, in the manufacture of a medicament for the treatment of a hematological cancer.

Combination Therapy

As discussed above, one aspect of the present invention is a method of treating cancer comprising administering to a patient in need thereof, a first amount of a histone deacetylase inhibitor, for example, a histone deacetylase inhibitor as described herein, for example, PXD-101, and a second amount of an other chemotherapeutic agent, for example, an other chemotherapeutic agent selected from: an antibody against VEGF, AVASTIN® (bevacizumab), an antibody against CD20, rituximab, bortezomib, thalidomide, dexamethasone, vincristine, doxorubicin, and melphalan, wherein the first and second amounts together comprise a therapeutically effective amount.

Another aspect of the present invention is a histone deacetylase inhibitor, for example, a histone deacetylase inhibitor as described herein, for example, PXD-101, for use in a method of treatment of a cancer, wherein said treatment comprises treatment with: (i) said histone deacetylase inhibitor and (ii) an other chemotherapeutic agent, for example, an other chemotherapeutic agent selected from: an antibody against VEGF, AVASTIN® (bevacizumab), an antibody against CD20, rituximab, bortezomib, thalidomide, dexamethasone, vincristine, doxorubicin, and melphalan.

Another aspect of the present invention is use of a histone deacetylase inhibitor, for example, a histone deacetylase inhibitor as described herein, for example, PXD-101, in the manufacture of a medicament for the treatment of cancer, wherein said treatment comprises treatment with: (i) said histone deacetylase inhibitor and (ii) an other chemotherapeutic agent, for example, an other chemotherapeutic agent selected from: an antibody against VEGF, AVASTIN® (bevacizumab), an antibody against CD20, rituximab, bortezomib, thalidomide, dexamethasone, vincristine, doxorubicin, and melphalan.

In some embodiments, the combination therapy results in a synergistic effect, for example, the HDAC inhibitor (e.g., PXD-101) and the other chemotherapeutic agent act synergistically, for example, in the inhibition of the proliferation of cancer cells, for example, multiple myeloma tumor cells.

The treatment procedures (e.g., treatment with histone deacetylase inhibitor, e.g., PXD-101; treatment with the other chemotherapeutic agent) can take place sequentially in any order, simultaneously, or a combination thereof.

For example, in one embodiment, the first treatment procedure (i.e., administration of a HDAC inhibitor), can take place prior to the second treatment procedure (i.e., administration of an other chemotherapeutic agent), after the second treatment procedure, at the same time as the second treatment procedure, or a combination thereof.

For example, the step of administering a first amount of a histone deacetylase inhibitor and the step of administering a second amount of an other chemotherapeutic agent can take place sequentially in any order, simultaneously or a combination thereof.

For example, in one embodiment, the step of administering a first amount of a histone deacetylase inhibitor occurs before the step of administering a second amount of an other chemotherapeutic agent.

For example, in one embodiment, the step of administering a first amount of a histone deacetylase inhibitor occurs after the step of administering a second amount of an other chemotherapeutic agent.

For example, in one embodiment, the step of administering a first amount of a histone deacetylase inhibitor and the step of administering a second amount of an other chemotherapeutic agent are simultaneous.

For example, a total treatment period can be decided for the HDAC inhibitor. The other chemotherapeutic agent can be administered prior to onset of treatment with the HDAC inhibitor or following treatment with the HDAC inhibitor. In addition, the other chemotherapeutic agent can be administered during the period of HDAC inhibitor administration but does not need to occur over the entire HDAC inhibitor treatment period.

One surprising and unexpected result disclosed herein is the ability of PXD-101 and AVASTIN® (bevacizumab) to act synergistically in the inhibition of the proliferation of ovarian tumor cells.

Accordingly, in one embodiment, the present invention relates to a method of treating cancer (e.g., a solid tumour cancer, e.g., ovarian cancer) comprising administering to a patient in need thereof, a first amount of PXD-101, and a second amount of AVASTIN® (bevacizumab), wherein the first and second amounts together comprise a therapeutically effective amount.

Another surprising and unexpected result disclosed herein is the ability of PXD-101 and rituximab to act synergistically in the inhibition of the proliferation of colon tumor cells and lymphoma cells.

Accordingly, in one embodiment, the present invention relates to a method of treating cancer (e.g., a hematological cancer, e.g., multiple myeloma) comprising administering to a patient in need thereof, a first amount of PXD-101, and a second amount of rituximab, wherein the first and second amounts together comprise a therapeutically effective amount.

Accordingly, in one embodiment, the present invention relates to a method of treating cancer (e.g., a solid tumour cancer, e.g., colon cancer) comprising administering to a patient in need thereof, a first amount of PXD-101, and a second amount of rituximab, wherein the first and second amounts together comprise a therapeutically effective amount.

Another surprising and unexpected result disclosed herein is the ability of PXD-101 and dexamethasone to act synergistically in the inhibition of the proliferation of multiple myeloma tumor cells.

Accordingly, in one embodiment, the present invention relates to a method of treating cancer (e.g., a hematological cancer, e.g., multiple myeloma) comprising administering to a patient in need thereof, a first amount of PXD-101, and a second amount of dexamethasone, wherein the first and second amounts together comprise a therapeutically effective amount.

In one embodiment, PXD-101 is administered to a subject for several days prior to the administration of dexamethasone. In another embodiment, the combination therapy is on a 21-day cycle wherein PXD-101 is administered every 24 hours for five days, then dexamethasone and PXD-101 are administered on days 2-5 and 10-13.

Another surprising and unexpected result disclosed herein is the ability of PXD-101 and bortezomib to act in an additive fashion in the inhibition of the proliferation of multiple myeloma tumor cells.

Accordingly, in one embodiment, the present invention relates to a method of treating cancer (e.g., a hematological cancer, e.g., multiple myeloma) comprising administering to a patient in need thereof, a first amount of PXD-101, and a second amount of bortezomib, wherein the first and second amounts together comprise a therapeutically effective amount.

In one embodiment, PXD-101 and bortezomib are administered simultaneously on at least day 1. In another embodiment, the PXD-101 is administered prior to bortezomib. In another embodiment, PXD-101 and bortezomib are administered on a 21-day cycle, for example, wherein PXD-101 is administered every 24 hours for the first five days, and then again on days 16-21 and bortezomib is administered on days 1, 4, 8 and 11.

The combination therapies described above can provide a therapeutic advantage in view of the differential toxicity associated with the individual treatment modalities. More specifically, treatment with HDAC inhibitors can lead to hematologic toxicity, whereas chemotherapy treatments can be toxic to tissue adjacent the tissue site. As such, this differential toxicity can permit each treatment to be preferably administered at a lower therapeutic dose, without increasing patient morbidity.

Inhibiting Cell Proliferation, Etc.

As discussed above, one aspect of the present invention is a method (e.g., an in vitro method, an in vivo method) for selectively inducing terminal differentiation, cell growth arrest and/or apoptosis of, or reducing the viability of, a neoplastic cell characteristic of hematological cancer, e.g., a myeloma cell, a plasmacytoma cell, or a plasma cell leukemia cell, wherein the method comprises contacting the neoplastic cell with an effective amount of an HDAC inhibitor, for example, a histone deacetylase inhibitor as described herein, for example, PXD-101.

Another aspect of the present invention is a method (e.g., an in vitro method, an in vivo method) of preventing, inhibiting (fully or partially), or arresting cell proliferation of a neoplastic cell characteristic of hematological cancer, e.g., a myeloma cell, a plasmacytoma cell, or a plasma cell leukemia cell, wherein the method comprises contacting the neoplastic cell with an effective amount of an HDAC inhibitor, for example, a histone deacetylase inhibitor as described herein, for example, PXD-101.

Another aspect of the present invention is a method (e.g., an in vitro method, an in vivo method) for selectively inducing terminal differentiation, cell growth arrest and/or apoptosis of, or reducing the viability of, a neoplastic cell, e.g., a neoplastic cell characteristic of hematological cancer, e.g., a myeloma cell, a plasmacytoma cell, or a plasma cell leukemia cell, wherein the method comprises contacting the neoplastic cell with a first amount of an HDAC inhibitor, for example, a histone deacetylase inhibitor as described herein, for example, PXD-101, and a second amount of an other chemotherapeutic agent, for example, an other chemotherapeutic agent selected from: an antibody against VEGF, AVASTIN® (bevacizumab), an antibody against CD20, rituximab, bortezomib, thalidomide, dexamethasone, vincristine, doxorubicin, and melphalan, wherein the first and second amounts together comprise an effective amount.

Another aspect of the present invention is a method (e.g., an in vitro method, an in vivo method) of preventing, inhibiting (fully or partially), or arresting cell proliferation of a neoplastic cell, e.g., a neoplastic cell characteristic of hematological cancer, e.g., a myeloma cell, a plasmacytoma cell, or a plasma cell leukemia cell, wherein the method comprises contacting the neoplastic cell with a first amount of an HDAC inhibitor, for example, a histone deacetylase inhibitor as described herein, for example, PXD-101, and a second amount of an other chemotherapeutic agent, for example, an other chemotherapeutic agent selected from: an antibody against VEGF, AVASTIN® (bevacizumab), an antibody against CD20, rituximab, bortezomib, thalidomide, dexamethasone, vincristine, doxorubicin, and melphalan, wherein the first and second amounts together comprise an effective amount.

In one embodiment, the amount of HDAC inhibitor is a contact concentration of from about 1 pM to about 50 µM such as, from about 1 pM to about 5 µM, for example, from about 1 pM to about 500 nM, such as from about 1 pM to about 50 mM, for example, 1 pM to about 500 pM. In one embodiment, the contact concentration is less than about 5.0 µM. In one embodiment, the contact concentration is about 500 nM. In one embodiment, the contact concentration is about 130 nM. In one embodiment, the contact concentration is about 100 nM.

In one embodiment, the method is practiced in vitro.
In one embodiment, the method is practiced in vivo.
In one embodiment, the neoplastic cell is a myeloma cell.
In one embodiment, the neoplastic cell is a plasmacytoma cell.
In one embodiment, the neoplastic cell is a plasma cell leukemia cell.
In one embodiment, the neoplastic is a transgenic cell.
In one embodiment, the neoplastic cell is in (or is part of) a subject (e.g., a living subject) such as a mammal, for example a human.

IV. Modes and Doses of Administration

As described above, one aspect of the present invention relates to a method of treating a hematological cancer comprising administering to a patient in need thereof a therapeutically effective amount of a histone deacetylase inhibitor, for example, a histone deacetylase inhibitor as described herein, for example, PXD-101.

As described above, one aspect of the present invention relates to a method of treating cancer comprising administering to a patient in need thereof, a first amount of a histone deacetylase inhibitor, for example, a histone deacetylase inhibitor as described herein, for example, PXD-101, and a second amount of an other chemotherapeutic agent, for example, an other chemotherapeutic agent selected from: an antibody against VEGF, AVASTIN® (bevacizumab), an antibody against CD20, rituximab, bortezomib, thalidomide, dexamethasone, vincristine, doxorubicin, and melphalan, wherein the first and second amounts together comprise a therapeutically effective amount.

The other chemotherapeutic agent (or agents, if more than one is employed) may be administered using conventional methods and protocols well known to those of skill in the art. For example, a typical dosage rate for AVASTIN® (bevacizumab) is 5 to 15 mg/kg, and a typical dosage rate for rituximab is 10 to 500 mg/m$^2$.

The HDAC inhibitor can be administered in an oral form, for example, as tablets, capsules (each of which includes sustained release or timed release formulations), pills, powders, granules, elixirs, tinctures, suspensions, syrups, and emulsions, all well known to those of ordinary skill in the pharmaceutical arts. Likewise, the HDAC inhibitor can be administered in intravenous (bolus or infusion), intraperitoneal, subcutaneous, or intramuscular form, well known to those of ordinary skill in the pharmaceutical arts.

The HDAC inhibitor can be administered in the form of a depot injection or implant preparation that can be formulated in such a manner as to permit a sustained release of the active ingredient. The active ingredient can be compressed into pellets or small cylinders and implanted subcutaneously or intramuscularly as depot injections or implants. Implants can employ inert materials such as biodegradable polymers or synthetic silicones, for example, Silastic, silicone rubber or other polymers manufactured by the Dow-Corning Corporation.

The HDAC inhibitor can also be administered in the form of liposome delivery systems, such as small unilamellar vesicles, large unilamellar vesicles and multilamellar vesicles. Liposomes can be formed from a variety of phospholipids, such as cholesterol, stearylamine, or phosphatidylcholines.

The HDAC inhibitor can also be delivered by the use of monoclonal antibodies as individual carriers to which the compound molecules are coupled.

The HDAC inhibitor can also be prepared with soluble polymers as targetable drug carriers. Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues.

Furthermore, the HDAC inhibitor can be prepared with biodegradable polymers useful in achieving controlled release of a drug, for example, polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacrylates, and cross linked or amphipathic block copolymers of hydrogels.

The dosage regimen utilizing the HDAC inhibitor can be selected in accordance with a variety of factors including type, species, age, weight, sex and the type of cancer being treated; the severity (i.e., stage) of the cancer to be treated; the route of administration; the renal and hepatic function of the subject; and the particular compound or salt thereof employed. An ordinarily skilled physician or veterinarian can readily determine and prescribe the effective amount of the drug required to treat, for example, to prevent, inhibit (fully or partially) or arrest the progress of the disease.

Oral dosages of the HDAC inhibitor, when used to treat the desired cancer, either alone or as part of combination therapy, can range between about 2 mg to about 2000 mg per day, such as from about 20 mg to about 2000 mg per day, such as from about 200 mg to about 2000 mg per day. For example, oral dosages can be about 2, about 20, about 200, about 400, about 800, about 1200, about 1600, or about 2000 mg per day. It is understood that the total amount per day can be administered in a single dose or can be administered in multiple dosing such as twice, three or four times per day.

For example, a subject can receive between about 2 mg/day to about 2000 mg/day, for example, from about 20 to about 2000 mg/day, such as from about 200 to about 2000 mg/day, for example from about 400 mg/day to about 1200 mg/day. A suitably prepared medicament for once a day administration can thus contain between about 2 mg and about 2000 mg, such as from about 20 mg to about 2000 mg such as from about 200 mg to about 1200 mg, such as from about 400 mg/day to about 1200 mg/day. The HDAC inhibitor can be administered in a single dose or in divided doses of two, three, or four times daily. For administration twice a day, a suitably prepared medicament would therefore contain half of the needed daily dose.

Intravenously or subcutaneously, the subject would receive the HDAC inhibitor (e.g., PXD-101) in quantities sufficient to deliver between about 3-1500 mg/m$^2$ per day, for example, about 3, 30, 60, 90, 180, 300, 600, 900, 1000, 1200, or 1500 mg/m$^2$ per day. Such quantities can be administered in a number of suitable ways, e.g., large volumes of low concentrations of HDAC inhibitor during one extended period of time or several times a day. The quantities can be administered for one or more consecutive days, intermittent days, or a combination thereof per week (7 day period). Alternatively, low volumes of high concentrations of HDAC inhibitor during a short period of time, e.g., once a day for one or more days either consecutively, intermittently, or a combination thereof per week (7 day period). For example, a dose of 300 mg/m$^2$ per day can be administered for 5 consecutive days for a total of 1500 mg/m$^2$ per treatment. In another dosing regimen, the number of consecutive days can also be 5, with treatment lasting for 2 or 3 consecutive weeks for a total of 3000 mg/m$^2$ and 4500 mg/m$^2$ total treatment.

Typically, an intravenous formulation can be prepared which contains a concentration of HDAC inhibitor of from about 1.0 mg/mL to about 10 mg/mL, e.g., 2.0 mg/mL, 3.0 mg/mL, 4.0 mg/mL, 5.0 mg/mL, 6.0 mg/mL, 7.0 mg/mL, 8.0 mg/mL, 9.0 mg/mL, or 10 mg/mL, and administered in amounts to achieve the doses described above. In one example, a sufficient volume of intravenous formulation can be administered to a subject in a day such that the total dose for the day is between about 300 and about 1200 mg/m$^2$.

In a preferred embodiment, 900 mg/m$^2$ of PXD-101 is administered intravenously every 24 hours for at least five consecutive days.

In one embodiment, PXD-101 is administered in a total daily dose of up to 1500 mg/m$^2$. In one embodiment, PXD-101 is administered intravenously in a total daily dose of 900 mg/m$^2$, for example, once daily, continuously (every day), or intermittently. In one embodiment, PXD-101 is administered intravenously in a total daily dose of 1000 mg/m$^2$, for example, once daily, continuously (every day), or intermittently. In one embodiment, PXD-101 is administered every day on days 1 to 5 every three weeks.

Glucuronic acid, L-lactic acid, acetic acid, citric acid, or any pharmaceutically acceptable acid/conjugate base with reasonable buffering capacity in the pH range acceptable for intravenous administration of the HDAC inhibitor can be used as buffers. Sodium chloride solution wherein the pH has been adjusted to the desired range with either acid or base, for example, hydrochloric acid or sodium hydroxide, can also be employed. Typically, a pH range for the intravenous formulation can be in the range of from about 5 to about 12. A preferred pH range for intravenous formulation wherein the HDAC inhibitor has a hydroxamic acid moiety (e.g., as in PXD-101), can be about 9 to about 12. Consideration should be given to the solubility and chemical compatibility of the HDAC inhibitor in choosing an appropriate excipient.

Subcutaneous formulations, preferably prepared according to procedures well known in the art at a pH in the range between about 5 and about 12, also include suitable buffers and isotonicity agents. They can be formulated to deliver a daily dose of HDAC inhibitor in one or more daily subcutaneous administrations, e.g., one, two or three times each day. The choice of appropriate buffer and pH of a formulation, depending on solubility of the HDAC inhibitor to be administered, is readily made by a person having ordinary skill in the art. Sodium chloride solution wherein the pH has been adjusted to the desired range with either acid or base, for example, hydrochloric acid or sodium hydroxide, can also be employed in the subcutaneous formulation. Typically, a pH range for the subcutaneous formulation can be in the range of from about 5 to about 12. A preferred pH range for subcutaneous formulation wherein the HDAC inhibitor has a hydroxamic acid moiety is about 9 to about 12. Consideration should be given to the solubility and chemical compatibility of the HDAC inhibitor in choosing an appropriate excipient.

The HDAC inhibitor can also be administered in intranasal form via topical use of suitable intranasal vehicles, or via transdermal routes, using those forms of transdermal skin patches well known to those of ordinary skill in that art. To be administered in the form of a transdermal delivery system, the administration will likely be continuous rather than intermittent throughout the dosage regime.

V. Pharmaceutical Compositions

The HDAC inhibitor can be administered as an active ingredient in admixture with suitable pharmaceutical diluents, excipients, or carriers (collectively referred to herein as "carrier" materials) suitably selected with respect to the intended form of administration, that is, oral tablets, capsules, elixirs, syrups and the like, and consistent with conventional pharmaceutical practices.

For example, in one embodiment, the pharmaceutical composition comprises the HDAC inhibitor PXD-101 in solution with L-arginine. To prepare this composition, a 10 g quantity of L-arginine was added to a vessel containing approximately 70 mL of Water-For-Injections BP. The mixture was stirred with a magnetic stirrer until the arginine had dissolved. A 5 g quantity of PXD-101 was added, and the mixture stirred at 25° C. until the PXD-101 had dissolved. The solution was diluted to a final volume of 100 mL using Water-For-Injections BP. The resulting solution had a pH of 9.2-9.4 and an osmolality of approximately 430 mOSmol/kg. The solution was filtered through a suitable 0.2 µm sterilizing (e.g., PVDF) membrane. The filtered solution was placed in vials or ampoules, which were sealed by heat, or with a suitable stopper and cap. The solutions were stored at ambient temperature, or, more preferably, under refrigeration (e.g., 2-8° C.) in order to reduced degradation of the drug.

In one embodiment, the HDAC inhibitor (e.g., PXD-101) can be administered orally. Oral administration can be in the form of a tablet or capsule. The HDAC inhibitor can be combined with an oral, non-toxic, pharmaceutically acceptable, inert carrier such as lactose, starch, sucrose, glucose, methyl cellulose, microcrystalline cellulose, sodium croscarmellose, magnesium stearate, dicalcium phosphate, calcium sulfate, mannitol, sorbitol and the like or a combination thereof. For oral administration in liquid form, the HDAC inhibitor can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, microcrystalline cellulose, sodium croscarmellose, polyethylene glycol, waxes and the like. Lubricants suitable for use in these dosage forms include sodium oleate, sodium stearate, magnesium stearate, sodium benzoate, sodium acetate, sodium chloride, and the like. Disintegrators suitable for use in these dosage forms include starch methyl cellulose, agar, bentonite, xanthan gum and the like.

Suitable pharmaceutically acceptable salts of the HDAC inhibitors described herein, and suitable for use in the method of the invention, are conventional non-toxic salts and can include a salt with a base or an acid addition salt such as a salt with an inorganic base, for example, an alkali metal salt (e.g., lithium salt, sodium salt, potassium salt, etc.), an alkaline earth metal salt (e.g., calcium salt, magnesium salt, etc.), an ammonium salt; a salt with an organic base, for example, an organic amine salt (e.g., triethylamine salt, pyridine salt, picoline salt, ethanolamine salt, triethanolamine salt, dicyclohexylamine salt, N,N'-dibenzylethylenediamine salt, etc.) etc.; an inorganic acid addition salt (e.g., hydrochloride, hydrobromide, sulfate, phosphate, etc.); an organic carboxylic or sulfonic acid addition salt (e.g., formate, acetate, trifluoroacetate, maleate, tartrate, methanesulfonate, benzenesulfonate, p-toluenesulfonate, etc.); a salt with a basic or acidic amino acid (e.g., arginine, aspartic acid, glutamic acid, etc.) and the like.

Kits

One aspect of the invention pertains to a kit or kit-of-parts comprising:

(a) a histone deacetylase (HDAC) inhibitor, such as PXD-101, preferably as a component of a pharmaceutically acceptable formulation, and preferably provided in a suitable container and/or with suitable packaging; and (b) another chemotherapeutic agent, preferably as a component of a pharmaceutically acceptable formulation, and preferably provided in a suitable container and/or with suitable packaging;

wherein said kit or kit-of-parts is suitable for use in a method for treating cancer.

In one embodiment, the kit or kit-of-parts further comprises instructions, e.g., written instructions, for use, for example, instructions for administration, e.g., of the two drugs. In one embodiment, the instructions include a list of indications (e.g., cancer, types of cancer) for which combination of drugs is a suitable treatment.

In one embodiment, the kit or kit-of-parts further comprises appropriate reagents (e.g., buffers, solvents) and devices (e.g., tubes, syringes) for assembly and use (e.g., administration).

The following examples more fully illustrate the preferred embodiments of the invention. They should in no way be construed, however, as limiting the broad scope of the invention, as described herein.

EXAMPLES

To measure the effects of HDAC inhibitors alone or in combination with chemotherapeutic agents on the proliferation of cancer cells, a variety of human multiple myeloma cell lines were grown in vitro and incubated with an HDAC inhibitor (i.e., PXD-101) alone or in combination with chemotherapeutic agents as described below. In addition, PXD-101 is used in clinical trials for the treatment of multiple myeloma either alone or in combination with dexamethasone or bortezomib. Additional studies employing a combination of PXD-101 with AVASTIN® (bevacizumab) (an antibody against CD20) or with rituximab (an antibody against VEGF) were also performed.

Example 1

Antiproliferative Activity of PXD-101 In Vitro

The effects of HDAC inhibitors on a variety of human multiple myeloma cell lines was tested in vitro to determine the potential clinical use of HDAC inhibitors (i.e., PXD-101) in the treatment of multiple myeloma.

CellTiter-Glo assays were used to assess the effects of PXD-101 on cell growth or viability of multiple myeloma cells in vitro. (See Table 1.) For example, six multiple myeloma cell lines (RPMI-8226, U266, EJM, LP-1, OPM-2 and KMS-12-BM) were used in the experiments. Cells were cultured, exposed to PXD-101 alone or in combination with a chemotherapeutic agent for a period of time, after which the number of viable cells was assessed using the CellTiter-Glo reagent from Promega (Madison, Wis.; Cat. No. G7572), as described below.

Cells were plated in 96-well plates at 3,000 cells/well in 90 µL of culture medium. The following day, various concentrations of PXD-101 alone or in combination with a chemotherapeutic agent were added in 10 µL/well and the cells were then incubated at 37° C. for 72 h. In some cases, cells were pretreated with chemotherapeutic agent for 6 hours prior to the addition of PXD-101. Subsequently, 50 µL/well of CellTiter-Glo reagent was added and the cells were shaken for 2 minutes and then incubated for an additional 10 minutes at room temperature. After the incubation time, luminescence (light) was measured in a luminometer.

The CellTiter-Glo assay measures the amount of ATP present, which in turn is proportional to cell number and viability. The CellTiter-Glo reagent utilizes an enzyme (luciferase) which catalyzes a light-liberating, ATP-dependent reaction in the presence of substrate (luciferin). An expansion in the number of viable cells results in an increase in the overall ATP levels which in turn is reflected by an increase in emitted light. If a drug inhibits cell growth or viability, this will be reflected by a decrease in emitted light, relative to untreated control cultures.

Percent activity (% activity), was calculated for each test compound as:

$$\% \text{ activity} = \{(S^c - B)/(S^\circ - B)\} \times 100$$

wherein $S^c$ denotes signal measured in the presence of the compound being tested, $S^\circ$ denotes signal measured in the absence of the compound being tested, and B denotes the background signal measured in blank wells containing medium only. The IC50 corresponds to the drug concentration which achieves 50% activity of untreated control cultures. IC50 values were calculated using the software package Prism 3.0 (GraphPad Software Inc., San Diego, Calif.) with variable slope option.

This example reports the effects of PXD-101 on six distinct multiple myeloma cell lines, three plasma cell leukemia cell lines and one plasmacytoma. The cells were incubated with PXD-101 for 72 hours in vitro, and their viability measured by the CellTiter-Glo assay. PXD-101 potently reduced the number of viable cells in this assay. The IC50 of PXD-101 ranged from 0.028 to 0.196 µM, and the average IC50 measured in the ten cell lines was 0.097 µM.

The following table summarizes the EC50 concentrations of PXD-101 in a variety of multiple myeloma cell lines, as well as various plasma cell leukemia cell lines and a plasmacytoma cell line.

TABLE 1

| Cell Line | Cell Line Details | PXD-101 IC$_{50}$ (µM) |
|---|---|---|
| RPMI-8226 | Multiple myeloma | 0.196 |
| U266 | Multiple myeloma | 0.141 |
| EJM | Multiple myeloma | 0.123 |
| LP-1 | MM; t(4; 14)(p16; q32) | 0.045 |
| OPM-2 | MM; t(4; 14)(p16; q32) | 0.106 |
| KMS-12-BM | MM; t(11; 14)(q13; q32) | 0.088 |
| AMO-1 | Plasmacytoma | 0.029 |
| L-363 | Plasma cell leukemia | 0.1 |
| SK-MM-2 | Plasma cell leukemia t(11; 14)(q13; q32) | 0.028 |
| KARPAS-620 | Plasma cell leukemia t(8; 14)(q24; q32) | 0.112 |
| | Mean | 0.097 |

Accordingly, this study identifies effective therapeutic concentrations of PXD-101 for use in clinical trials for the treatment of multiple myeloma cell, plasma cell leukemia, and plasmacytoma.

Example 2

Combination Studies

The effects of HDAC inhibitors in combination with standard chemotherapeutic agents were tested in vitro to determine the potential clinical use of an HDAC inhibitor (i.e., PXD-101), in combination with various chemotherapeutic agents (i.e., vincristine, doxorubicin, melphalan, dexamethasone).

Wst-1 proliferation assays were used to assess the antiproliferative effects of drug combinations. The cell lines used in these experiments are shown in Table 2. Four myeloma cell lines (e.g., JJN3, LP-1, RPMI-8226, U266) were used in the combination studies. A commercial program, CalcuSyn, was employed to determine whether the combined effects are synergistic, antagonistic, or additive.

Cells were cultured, exposed to PXD-101 alone or in combination with a chemotherapeutic agent, and incubated for a time, and the number of viable cells was then assessed using the Cell Proliferation Reagent WST-1 from Boehringer Mannheim (Cat. No. 1 644 807), described below.

Cells were plated in 96-well plates at 3-10×10$^3$ cells/well in 100 µL of culture medium. The following day, different concentrations of PXD-101 alone or in combination with a chemotherapeutic agent were added and the cells incubated at 37° C. for 48 hours. Subsequently, 10 µL/well of WST-1 reagent was added and the cells re-incubated for 1 hour. After the incubation time, absorbance was measured.

WST-1 is a tetrazolium salt which is cleaved to formazan dye by cellular enzymes. An expansion in the number of viable cells results in an increase in the overall activity of mitochondrial dehydrogenases in the sample. This augmentation in the enzyme activity leads to an increase in the amount of formazan dye formed, which directly correlates to the number of metabolically active cells in the culture. The formazan dye produced is quantified by a scanning multiwell spectrophotometer by measuring the absorbance of the dye solution at 450 nm wavelength (reference wavelength 690 nm).

Percent activity (% activity) in reducing the number of viable cells was calculated for each test compound as:

$$\% \text{ activity} = \{(S^c - B)/(S^\circ - B)\} \times 100$$

wherein $S^c$ denotes signal measured in the presence of the compound being tested, $S^\circ$ denotes signal measured in the absence of the compound being tested, and B denotes the background signal measured in blank wells containing medium only. The IC50 corresponds to the concentration which achieves 50% activity. IC50 values were calculated using the software package Prism 3.0 (GraphPad Software Inc., San Diego, Calif.), setting top value at 100 and bottom value at 0.

Measurement of cell viability in the presence of increasing concentration of test compound at different time points is used to assess both cytotoxicity and the effect of the compound on cell proliferation.

The results were further analyzed using the Combination Index (CI) method with the "CalcuSyn" program from Biosoft. A CI value of less than 1 indicates synergy, 1 indicates an additive effect, and greater than 1 indicates antagonism.

Using the CalcuSyn program, the CI is determined by the isobologram equation CI=(D)1/(Dx)1+(D)2/(Dx)2. Drug 1 (D)1 and drug 2 D(2) in combination inhibit X % and (Dx)1 and (Dx)2 are the doses of drug 1 and drug 2 alone that also inhibits X %. For each compound, the % growth values at each dose as determined in the Wst-1 assay are used. CI values that are less than 0.3 are very synergistic, those between 0.3-0.7 are synergistic, those between 0.7-1 are additive, and those greater than 1 are antagonistic. CI's are compared at various percent inhibitory concentrations.

PXD-101+Dexamethasone

The anti-proliferative effects of adding PXD-101 simultaneously (e.g., 48 hour co-incubations), 24 hours after, or 24 hours before adding the chemotherapeutic agent, dexamethasone to the JJN3, LP-1, RPMI-8226, and U266 tumor cell lines were also examined by the methods described above.

When cells were treated with PXD-101 in combination with dexamethasone simultaneously (i.e., at 48 hour co-incubations), 24 hour PXD-101 then 48 hour PXD-101+DEX, or 24 hour DEX, then 48 hour PXD-101+DEX, synergistic effects were obtained for the LP-1 and U266 tumor cell lines over a range of concentrations (see Table 2). Strong synergy (CI<0.3) was observed in the U266 cell line when PXD-101 was administered for 24 hours, followed by 48 hour PXD-101+DEX, and in the LP1 cell line when DEX was administered for 24 hours, followed by 48-hour co-incubation of PXD-101 and DEX over a range of concentrations and conditions (see Table 2).

PXD-101+Doxorubicin

The myeloma cell lines (e.g., JJN3, LP-1, RPMI-8226, U266) were treated with PXD-101 and doxorubicin. As described above, the combined effects of these compounds on the myeloma cell lines was determined by plotting isobolograms and calculating combination indices.

Additive to synergistic effects were observed for this combination when PXD-101 and doxorubicin were co-incubated for 48 hours over a range of concentrations (see Table 2).

This example reports the effect of combining PXD-101 with standard chemotherapeutics. There is strong synergy between PXD-101 and DEX when U266 cells are incubated with PXD-101 for 24 hours prior to the administration of DEX, and when LP1 cells are incubated with DEX for 24 hours prior to the administration of PXD-101 over a range of concentrations and conditions (See Table 2).

Combination of PXD-101 with doxorubicin on myeloma cell lines produced additive to synergistic effects when the compounds were co-incubated over a range of concentrations and conditions (See Table 2).

The following table summarizes the Combination Indices (CI) resulting from combination treatment with PXD-101 and four chemotherapeutic agents (i.e., vincristine, doxorubicin, melphalan, dexamethasone) using three different incubation schedules on four myeloma cell lines.

At least three points fall on or below CI value corresponding to:

| | | |
|---|---|---|
| +++ | Very synergistic | CI <0.3 |
| ++ | Synergistic | CI 0.3-0.7 |
| + | Additive | CI 0.7-1 |
| − | Antagonistic | CI >1 |
| nd | Not done | |

PXD-101+Rituximab

The B-cell lymphoma cell lines SU-DHL-4, Raji and RAMOS were treated with PXD-101 and rituximab. The combined effects of these compounds on the cell lines were determined by plotting isobolograms and calculating combination indices, as described above for the myeloma cell lines. As shown in FIG. 5 for the SU-DHL-4 cell line, additive to synergistic effects were observed for this combination when PXD-101 and rituximab were co-incubated for 48 hours over a range of concentrations.

Accordingly, the above combination studies identify effective therapeutic combinations for use in clinical trials of PXD-101.

Example 3

Antiproliferative Activity of PXD-101 in Combination with Bortezomib In Vitro

The effects of HDAC inhibitors in combination with the chemotherapeutic agent bortezomib was tested in vitro to determine the potential clinical use of an HDAC inhibitor (i.e., PXD-101 or SAHA), in combination chemotherapy.

Figure 2:
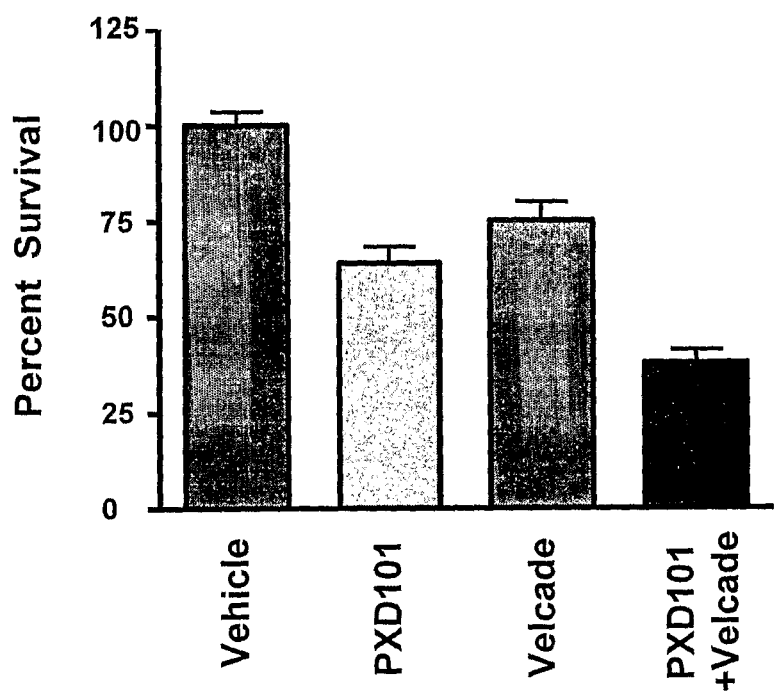
FIG. 2 depicts a graph showing the survival rates of a multiple myeloma cell line (U266) upon treatment with PXD-101, bortezomib, or both.
Figure 3:
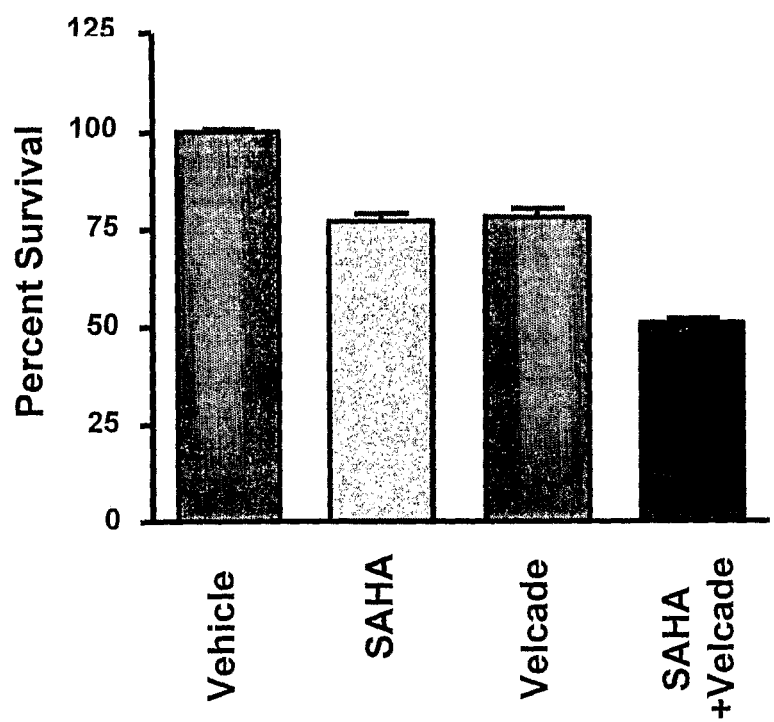
FIG. 3 depicts a graph showing the survival rates of a multiple myeloma cell line (U266) upon treatment with PXD-101, SAHA, or both.

CellTiter-Glo cell viability assays (as described above) were used to assess the anti-proliferative effects of PXD-101 in combination with bortezomib (FIG. 2). For comparison, the anti-proliferative effects of SAHA in combination with bortezomib were measured (FIG. 3). The multiple myeloma cell line U266 was used in the combination studies. U266 cells were treated with bortezomib at 1 nM for 6 hours, followed by a cotreatment for 72 hours with a combination of bortezomib at 1 nM and PXD-101 at 130 nM (FIG. 2). Similarly, U266 cells were treated with bortezomib at 1 nM for 6 hours, followed by a cotreatment for 72 hours with a combination of bortezomib at 1 nM and SAHA at 130 nM (FIG. 3). In control experiments, either PXD-101, SAHA or bortezomib were omitted.

TABLE 2

Summary of Myeloma Combination Studies with PXD-101 in vitro

| | PXD-101 combined with: | | | |
|---|---|---|---|---|
| Cell Line | Vincristine | Doxorubicin | Melphalan | Dexamethasone |
| JJN3 | −(1), +(2), ++(3) | +(1), −(2, 3) | +(1, 2), ++(3) | −(2) |
| LP-1 | −(2), +(1, 3) | ++(1), −(2, 3) | −(1, 3), +(2) | ++(1, 2), +++(3) |
| RPMI-8226 | ++(1), −(2, 3) | +(1, 2), ++(3) | +(1, 2), ++(3) | +(2) |
| U266 | +(1), −(2, 3) | ++(1), +(2), −(3) | +(1, 3), ++(2) | +++(2), ++(3) |

Notes for Table:
Numbers in brackets is a guide to the schedule used in each experiment (see below).
Results in Table are those produced using "standard" combination protocol.
(1) 48 hour co-incubations.
(2) 24 hour PXD-101 then 48 hour PXD-101 & compound.
(3) 24 hour compound then 48 hour PXD-101 & compound.

When U266 were pre-treated with bortezomib, then co-treated with bortezomib and PXD-101 as described above, the effect on proliferation was greater than with either drug alone (FIG. 2). Co-treatment with bortezomib and PXD-101 resulted in at least an additive effect.

When U266 were pre-treated with bortezomib, then co-treated with bortezomib and SAHA as described above (FIG. 2), the effect on proliferation was smaller than with the bortezomib/PXD-101 combination (FIG. 3). Furthermore, when U266 cells were treated with PXD-101 alone, the effect on proliferation (FIG. 2) was greater than when U266 cells were treated with SAHA alone (FIG. 3). Hence, PXD-101 in combination with bortezomib inhibited proliferation more potently than SAHA in combination with bortezomib. In addition, PXD-101 alone inhibited proliferation more potently than SAHA alone.

Accordingly, the study described in Example 3 identifies effective therapeutic concentrations and combinations of PXD-101 and bortezomib for use in clinical trials.

Example 4

Clinical Trial: PXD-101 Monotherapy, and PXD-101+DEX Combination Therapy

Primary Objective

The primary objective of this study is to assess in patients with advanced myeloma the efficacy of PXD-101 treatment as measured by response rate (CR, PR, MR, NC/SD, PD) using the response criteria of Bladé et al. (Br. J. Haematol., 1998, vol. 102, pp. 1115-1123).

Secondary Objectives

Secondary objectives of this study are to examine time to response, duration of response, time to progression, time to next therapy, and survival following single agent PXD-101 therapy; and to examine safety following single agent PXD-101 therapy.

Objectives in Respect of Patients not Achieving CR, PR or MR Following Two Cycles of PXD-101 Monotherapy (Part B):

Objectives in this respect include: to examine the chemotherapy sensitizing effect of PXD-101 by assessing the efficacy (response rate, duration of response, time to progression and survival) and safety of a combination of dexamethasone and PXD-101; to determine the pharmacokinetic parameters for PXD-101 following intravenous administration in monotherapy and in the dexamethasone combination on day 1 and 4; to investigate the pharmacodynamic effects of PXD-101 in blood mononuclear cells on day 1 and 4 and when possible in tumor biopsies (bone marrow).

Trial Design

An open-label, non-randomized, multi-centered, phase II trial to assess the efficacy and safety of PXD-101 monotherapy, and the assessment in non-responders of the efficacy and safety of PXD-101 in combination with dexamethasone. Approximately 50 evaluable patients are included.

Patient Main Selection Criteria

Patients of age≥18 years with confirmed diagnosis of multiple myeloma (see below for diagnostic criteria) in patients who have failed two prior lines of therapy.

Diagnostic Criteria for Multiple Myeloma

A. Monoclonal immunoglobulin (M-component) in serum of IgG-type>30 g/L, of IgA type>20 g/L, of IgD type or IgE type of any concentration and/or excretion of M-component in the urine of type k or I type>1 g/24 hours.

B. M-component in serum and/or urine in lower concentration than indicated above in 'A'.

C. 10% or more plasma cells in bone marrow aspirate or plasmocytosis in biopsy from bone marrow or soft tissue tumor.

D. Osteolytical bone lesions.

The diagnosis of multiple myeloma demands one of the following combinations: A+C, A+D, or B+C+D.

Evaluable Disease (as Defined Above).

Adequate bone marrow and hepatic functions. Total bilirubin≤1.5×upper normal limit. AST (SGOT), ALT (SGPT)≤2.5×upper normal limit. Performance status (PS)≤2 (ECOG scale). Estimated life expectancy greater than 3 months. Female patients with reproductive potential with a negative serum pregnancy test within the last 7 days before trial enrollment and use a safe contraceptive during and in a period of 60 days after the trial. Fertile female partners to male participants must likewise use contraceptive.

PXD-101 Product

The drug product PXD-101 (50 mg/mL) injection contains 10 mL of a sterile, clear yellow solution of 50 mg/mL of PXD-101 and 100 mg/mL L-Arginine, Ph. Eur. in Water-for-Irrigation, Ph. Eur. at a pH of 9.0-99. The product needs to be diluted with 9.9% saline, or 5% glucose before infusion.

PXD-101 Preparation and Administration

The individual dosage is based on body surface area. The calculated dose is drawn from the PXD-101 vial, added to a 250 mL bag of isotonic glucose for infusion and infused intravenously (IV) over 30 minutes. Treatment will be given once daily according to the assigned schedule.

Dexamethasone Delivery, Preparation and Administration

The standard dose of dexamethasone, 40 mg/day is to be administered orally as 5 tablets of 8 mg. On the treatment days where PXD-101 is also administered intravenously (IV), the dexamethasone is administered 2 hours after the PXD-101 dose.

Treatment Dose and Schedule—Initial Study Part A

PXD-101 is administered as a 30-minute intravenous (IV) infusion of 900 mg/m$^2$/d, in the first cycle. The treatment is given every 24 hours (±2 hours) for 5 consecutive days, followed by 2 weeks of observation. This is cycle 1.

Cycle 2 begins on day 22 (study day 22) with a second 5-day cycle of treatment with PXD-101, followed by 2 weeks of observation. During study week 6 (cycle 2, day 15-21) patients will undergo evaluation tests for determination of response. Response will be assigned on study day 43 as CR, PR, MR, SD, PD based on the test results from the previous week and treatment will continue as follows:

All patients as a minimum receive 2 cycles of PXD-101 monotherapy. At the end of the two cycles the patients are evaluated for response. Based on the patient's response as assigned on study day 43, treatment will continue in Study Part A continued or Study Part B as follows:

Patients in CR, PR or MR will continue PXD-101 monotherapy in Study Part A until progression or until receipt of a maximum of 8 cycles including the two initial cycles. Patients whose response is NC/SD, PD will begin Study Part B, PXD-101 plus dexamethasone, as described in the following section.

Treatment Dose and Schedule—Study Part B

Patients with responses of SD or PD following two cycles of PXD-101 monotherapy as assessed after the second treatment cycle continue therapy with a combination of PXD-101 as infused in cycles 1 and 2 with the addition of dexamethasone 40 mg orally daily on days 2-5 and days 10-13. Patients in Study Part B receive a minimum of two cycles of combined therapy. Patients who respond to this combination may continue the treatment until progression or completion of a total of 8 cycles including the initial two cycles.

Example 5

Clinical Trial: Combination therapy of PXD-101 with Bortezomib

The primary objectives of this study were: (i) to determine the maximum tolerated dose (MTD) and the dose-limiting toxicities (DLT) of PXD-101 administered in combination with bortezomib; (ii) to establish the dose of each drug recommended for a future Phase II protocol with the combination; (iii) to explore anti-tumor activity of the combination of PXD-101 plus bortezomib in patients with relapsed/refractory multiple myeloma.

The secondary objectives were: (i) to compare the pharmacodynamics (histone acetylation) of PXD-101 in the presence and absence of bortezomib; (ii) to determine the pharmacodynamics (proteasome inhibition) of bortezomib in the presence and absence of PXD-101; and (iii) to determine the pharmacokinetics of PXD-101 when given in combination with bortezomib.

The trial is an open-label, multi-center, dose-escalation safety, pharmacokinetic, and pharmacodynamic study in patients with relapsed/refractory multiple myeloma that have failed at least 2 prior lines of therapy, with an expansion arm at the MTD to confirm safety and assess anti-tumor activity, pharmacokinetics, and pharmacodynamics, and the same multiple myeloma patient population.

A total of up to 45 patients are enrolled for the study enrollment, with ~30 patients in the dose escalation arm and up to 15 patients in the MTD expansion arm. Patients are treated with PXD-101 intravenously (IV) (30 minute infusion) daily on Days 1-5 and with bortezomib intravenously (IV) (3-5 second push) on Days 1, 4, 8, and 11, in 21-day cycles. PXD-101 infusion starts ~1 hour after bortezomib administration. Dose escalation ranges from 300-900 mg/m². PXD-101 and 0.7-1.6 mg/m² bortezomib, occurs in successive cohorts, until the MTD of the combination is established.

Once the MTD for the combination of PXD-101 and bortezomib has been established, up to 15 additional patients with relapsed/refractory multiple myeloma are enrolled at the combination MTD to confirm safety, PK and PD, and to assess anti-tumor activity. Thus approximately 20 patients are dosed at the MTD, including 3-6 patients in the escalation arm. In the MTD expansion phase, dose scheduling is the same as in the dose escalation arm.

Pharmacokinetic and pharmacodynamic analyses are performed in Cycle 1. For PXD-101, PK and PD are analyzed on Days 3 and 4 (days without and with bortezomib administration), and for bortezomib, PD analysis will be on Days 4 and 8 (days with and without PXD-101 administration). Pharmacodynamic assessment of PXD-101 occurs by measurement of histone acetylation in peripheral blood cells, while for bortezomib, inhibition of 20S proteasome is measured. Anti-tumor activity is assessed in all patients after two cycles, and every cycle thereafter, using the Blade criteria (Blade 1998). All patients enrolled in the study receive both drugs until disease progression as measured using the Blade criteria, for up to eight cycles, or until development of significant treatment related toxicities.

The following patient selection criteria was employed: patients≥18 years of age with a confirmed diagnosis of multiple myeloma (criteria described by International Myeloma Working Group [IMWG, 2003]). Relapsed after or failed at least two prior lines of therapy for multiple myeloma. Karnofsky performance>70%. Life expectancy of at least 3 months. Acceptable liver function (Bilirubin≤1.5 times upper limit of normal (ULN); AST (SGOT), ALT (SGPT) and Alkaline phosphatase≤2.5 times ULN). Acceptable hematologic status (ANC≥1500 cells/mm3; Platelet count≥100,000 (plt/mm3); Hemoglobin≥9 g/dL). Serum potassium within normal range. For men and women of child-producing potential, the use of effective contraceptive methods during the study.

Example 6

Evidence of Tumor Reduction in Humans

A Phase 1 open label, dose escalation, safety, pharmacokinetics (PK), and pharmacodynamics (PD) study of PXD-101 was conducted in patients with advanced cancers.

PXD-101 was administered as a 30-minute intravenous (IV) infusion daily for 5-days every 3-weeks. In a subgroup of patients, PXD-101 was administered orally once, twice or thrice on day 1 only, in course 2 or 3. Acetylation of histones extracted from peripheral blood mononuclear cells (PB-MNC) was measured by Western blotting. The PK/PD profile of intravenous and oral PXD-101 was evaluated.

The results of this study are as follows: 34 patients (median age 58 years, range 28-74; 19 male, all ECOG PS≤2) have been treated with a total of 103 cycles of PXD-101 (median 2; range 1 to 13) at 6 dose levels: 150 mg/m² (4 patients), 300 mg/m² (4 patients), 600 mg/m² (6 patients), 900 mg/m² (3 patients), 1000 mg/m² (12 patients) and 1200 mg/m² (5 patients). Dose limiting toxicity was reported in 3 patients: G3 fatigue (1 patient) at 600 mg/m², short-lived atrial fibrillation (1 patient) at 1200 mg/m² and G3 diarrhea and lethargy (1 patient) at 1200 mg/m². The most commonly reported other adverse events (all grade ½) included: fatigue, nausea, vomiting, constipation, diarrhea and injection site reactions.

PXD-101 PK was dose-proportional. The terminal elimination half-life ranged between 30 and 60 minutes, apart from one patient with a $t_{1/2}$ of 1.8 hours. There was no drug accumulation on repeated IV dosing. $C_{max}$ (range 6.5-55.8 µg/ml) was reached at the end of the infusion, as was histone H4 hyperacetylation with the latter being sustained for 4-24 hours in a dose-dependent manner. The mean single dose oral bioavailability was 33%. For b.i.d. (1000 mg/m²) oral dose administration on a single day in 5 patients, $C_{max}$ was 1.1-2.9 µg/mL, $t_{1/2}$ was 1.5-2.0 hours, mean oral bioavailability was 42.8% with SD 12.5%. Oral administration of PXD-101 at 1000 mg/m² maintained histone acetylation 40-50% above baseline for 5-10 hours. For t.i.d. (1000 mg/m²) oral dose administration on a single day in 2 patients, $C_{max}$ was 1.3-1.8 µg/mL, $t_{1/2}$ was 2.0-2.6 hours and oral bioavailability was 28% and 70%. There was no accumulation with 12-hour interval dosing, but a tendency towards accumulation with 8-hour interval dosing. Accrual is now continuing with patients receiving oral dosing (1000 mg/m²) once daily for 5-days.

A patient with epithelial mediastinal thymoma had a 70% reduction of her mediastinal disease and has been on the study for over 1-year. A favorable outcome was also observed in a patient with metastatic alveolar sarcoma.

Accordingly, in view of the above, it was concluded that the HDAC inhibitor PXD-101 is well tolerated utilizing a once daily for 5-days 30-minute intravenous (IV) infusion with an MTD of 1000 mg/m². PXD-101 is orally bioavailable and well tolerated when administered by once, twice or thrice daily dosing on a single day.

Example 7

AVASTIN® (Bevacizumab) and PXD-101

The object of this study was to investigate the tumour growth inhibitory effect of AVASTIN® (bevacizumab) in an A2780 ovarian cancer subcutaneous xenograft model. Mice were treated on day 4 with AVASTIN® (bevacizumab) (5 mg/kg). The chemosensitising effect of PXD-101 in combination with AVASTIN® (bevacizumab) was also investigated. AVASTIN® (bevacizumab) caused significant growth inhibition in A2780 xenograft in mice. FIG. 4 shows that PXD-101 given on days 0-8, 0-4 or 4-8 showed synergy with AVASTIN® (bevacizumab), demonstrating a significant chemosensitizing effect.

Those skilled in the art will recognize, or be able to ascertain using no more than routine experimentation, many equivalents to the specific embodiments of the invention described herein. Such equivalents are intended to be encompassed by the following claims.

Thus, while the preferred embodiments of the invention have been illustrated and described, it is to be understood that this invention is capable of variation and modification, and should not be limited to the precise terms set forth. The inventors desire to avail themselves of such changes and alterations which may be made for adapting the invention to various usages and conditions. Such alterations and changes may include, for example, different pharmaceutical compositions for the administration of the therapeutic agents according to the present invention to a mammal; different amounts of therapeutic agents in the compositions to be administered; different times and means of administering the therapeutic agents according to the present invention; and different materials contained in the administration dose including, for example, combinations of different therapeutic agents, or combinations of the therapeutic agents according to the present invention together with other biologically active compounds for the same, similar or differing purposes than the desired utility of those therapeutic agents specifically disclosed herein. Such changes and alterations also are intended to include modifications in the chemical structures of the therapeutic agents described herein in which such changes alter the agents in a manner as not to change the desired potential of the therapeutic agents, but as to change solubility of the therapeutic agents in the pharmaceutical composition to be administered or in the body, absorption of the therapeutic agents by the body, protection of the therapeutic agents for either shelf life or within the body until such time as the biological action of the therapeutic agents is able to bring about the desired effect, and such similar modifications. Accordingly, such changes and alterations are properly intended to be within the full range of equivalents, and therefore within the purview of the following claims.

The invention and the manner and process of making and using it have been thus described in such full, clear, concise and exact terms so as to enable any person skilled in the art to which it pertains, or with which it is most nearly connected, to make and use the same.

The invention claimed is:

1. A method of killing a B-cell lymphoma cell comprising contacting a B-cell lymphoma cell with,
a first amount of a histone deacetylase inhibitor, and
a second amount of an antibody against CD20,
wherein the first and second amounts together comprise an amount effective to kill the B-cell lymphoma cell, and wherein the amount effective to kill the B-cell lymphoma cell has a synergistic effect compared to the effect of the first amount alone or the effect of the second amount alone;
wherein the histone deacetylase inhibitor is a compound of formula:

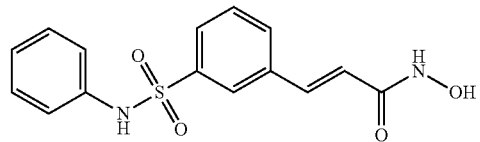 [SMILES: O=C(/C=C/c1cccc(S(=O)(=O)Nc2ccccc2)c1)NO]

or a pharmaceutically acceptable salt thereof; and
wherein the antibody against CD20 is rituximab or an anti-CD20 antibody that binds to the same epitope on CD20 that is bound by rituximab.

2. The method according to claim 1, wherein the lymphoma is a Hodgkin's lymphoma.

3. The method according to claim 1, wherein the lymphoma is a non-Hodgkin's lymphoma.

* * * * *